ns Patent [19]

Castelhano et al.

[11] Patent Number: 4,929,630
[45] Date of Patent: May 29, 1990

[54] TRANSGLUTAMINASE INHIBITORS

[75] Inventors: Arlindo L. Castelhano, Mississauga, Canada; Lawrence M. DeYoung, Half Moon Bay, Calif.; Alexander Krantz, Toronto, Canada; Diana H. Pliura, Mississauga, Canada; Michael C. Venuti, San Francisco, Calif.

[73] Assignee: Syntex (U.S.A.) Inc., Palo Alto, Calif.

[21] Appl. No.: 404,791

[22] Filed: Sep. 8, 1989

Related U.S. Application Data

[60] Division of Ser. No. 25,451, Mar. 13, 1987, Pat. No. 4,912,120, which is a continuation-in-part of Ser. No. 839,743, Mar. 14, 1986, abandoned.

[51] Int. Cl.$^5$ .................. A61K 31/44; A61K 31/445; A61K 31/42; C07D 261/04
[52] U.S. Cl. .................................. 514/380; 514/326; 514/340; 514/378; 514/859; 514/863; 546/209; 546/275; 548/240; 548/243
[58] Field of Search ............... 514/326, 378, 380, 859, 514/863, 340

[56] References Cited

U.S. PATENT DOCUMENTS

| | | | |
|---|---|---|---|
| 4,276,299 | 6/1981 | Della Bella et al. | 514/378 |
| 4,277,485 | 7/1981 | Durant et al. | 514/374 |
| 4,283,403 | 8/1981 | Davenport | 514/340 |
| 4,298,744 | 11/1981 | Kelly et al. | 548/240 |
| 4,451,476 | 5/1984 | Diana | 514/378 |
| 4,497,812 | 2/1985 | Creuzet et al. | 514/211 |
| 4,499,090 | 2/1985 | Creuzet et al. | 514/210 |

FOREIGN PATENT DOCUMENTS

| | | |
|---|---|---|
| 16255 | 10/1980 | European Pat. Off. . |
| 4869M | 11/1965 | France . |
| 4213307 | 7/1967 | Japan . |
| 8101145 | 4/1981 | World Int. Prop. O. . |

OTHER PUBLICATIONS

P. A. Wade et al., Tetrahedron Letters, vol. 23, (No. 44), 4563–4566 (1982), Cyanogen Chloride n–Oxide Cycloadditions, A Simple Short Route to AT-125.
Chemical Abstracts, vol. 78, (No. 13), Apr. 2, 1973, p. 466, Abstract No. 84476f.
Schasteen et al., "The Binding Mechanism of Glutathione and the Anti-Tumor Drug . . . ", Biochemical and Biophysical Res. Comm., 112(2), 564–70 (1983).
Tso et al., "Mechanism of Inactivation of Glutamine Amidotransferases by the Antitumor Drug . . . ," J. Biol. Chem., 255(14), 6734–38 (1980).
McGuire et al., "Phase II Trial of Acivivin in Patients with Advanced Epithelial Ovarian Carcinoma", Investigational New Drugs, 4, 49–52 (1986).
Lui et al., "Biochemical Pharmacology of Acivicin in Rat Hempatoma Cells", Biochem. Pharmacology, 31(21), 3469–73 (1982).
Poster et al., "Acivicin", Cancer Clin. Trials, 4, 327–30 (1981).
Maroun et al., "Phase II Study of Acivicin in Colorectal Carcinoma", Cancer Treatment Reports, 68(9), 1121–23 (1984).
Jayaram et al., "Mechanism of Resistance of a Variant of P388 Leukemia to . . . ," Cancer Research, 45, 207–12 (1985).
Denton et al., "Rapid in Vivo Inactivation by Acivicin of CTP Synthesase . . . ," Life Sciences, 30(13), 1073–80 (1982).
McGovren et al., "Pharmacokinetic and Biochemical Studies on Acivicin in Phase I Clinical Trials", cancer Research 45, 4460–63 (1985).
"Information Update", Drugs of the Future, 8(4), 351–54 (1983).
"Information Update", Drugs of the Future, 4(4), 252–54 (1979).
Martin et al., "Derivatization and Purification of Acivicin", The J. of Antibiotics, 34(4), 459–61 (1981).
Capraro et al., "The Use of Acivicin in Determination of Rate Constants for Turnover of Rat Renal . . . ," J. Biological Chem., 260(6), 3408–12 (1985).
Jayaram et al., "Mechanism of Resistance of a Variant of P388 Leukemia to . . . ," Cancer Research, 45, 207–12 (1985).
Weber et al., "Control of Enzymic Programs and Nucleotide Pattern in Cancer Cells by Activicin and Tiazofurin", Adv. in Enzyme Regulation, 22, 69–93 (1984).
Earhart et al., "Acivicin in 1985", Adv. in Enzyme Regulations, 24, 179–243 (1986).
Carl et al., "Protease-Activated Prodrugs for Cancer Chemotherapy", Proc. Natl. Acad. Sci. U.S.A., 77(4), 2224–28 (1980).
Chakravarty et al., "Plasmin-Activated Prodrugs for Cancer Therapy", J. Med. Chem., 26, 638–44 (1983).
Wade et al., "Benzenesulfonyl Carbonitrile Oxide", Tetrahedron, 40(3), 601–11 (1984).
De Young et al., "Tranglutaminase Activity in Human and Rabbit Ear Comedogenesis", J. of Invest. Dermatology, 82(3), 275–79 (1984).
Abstract of U.S. Pat. No. 3,090,788 (Derwent Abs. No. 7639f).
Abstract of Japanese Kokoku No. 9143/67 (Derwent Abs. No. 26790F).
Abstract of Japanese Kokoku No. 9145/67 (Derwent Abs. No. 26792F).
Abstract of Japanese Kokoku No. 9830/67 (Derwent Abs. No. 26974F).

(List continued on next page.)

Primary Examiner—Cecilia Shen
Attorney, Agent, or Firm—Lester E. Johnson; Tom M. Moran; Alan M. Krubiner

[57] ABSTRACT

The present invention is directed to certain 3,5 substituted, 4,5-dihydroisoxazoles, and methods for their use. These compounds are transglutaminase inhibitors, and are particularly effective in the inhibition of epidermal transglutaminase and the treatment of acne.

13 Claims, No Drawings

OTHER PUBLICATIONS

Abstract of Japanese Kokai No. 123061/74 (Derwent Abs. No. 16812W).
Abstract of DT Patent No. 2514984 (Derwent Abs. No. 74374W).
Abstract of Japanese Kokai No. 112371/79 (Derwent Abs. No. 19044B).
Abstract of Japanese Kokai No. 44665/79 (Derwent Abs. No. 37963B).
Abstract of Japanese Kokai No. 73773/79 (Derwent Abs. No. 55096B).
Abstract of BE Patent No. 867261 (Derwent Abs. No. 84158B).
Abstract of U.S. Pat. No. 4,188,324 (Derwent Abs. No. 14626C).
Abstract of U.S. Pat. No. 4,232,164 (Derwent Abs. No. 84300C).
Abstract of U.S. Pat. No. 4,256,898 (Derwent Abs. No. 25346C).
Abstract of U.S. Pat. No. 4,275,213 (Derwent Abs. No. 51607D).
Abstract of U.S. Pat. No. 4,275,214 (Derwent Abs. No. 51608D).
Abstract of BE Patent No. 887954 (Derwent Abs. No. 71771D).
Abstract of U.S. Pat. No. 4,298,744 (Derwent Abs. No. 87203D).
Abstract of EP Patent No. 81783 (Derwent Abs. No. 61633K).
Abstract of EP Patent No. 114993 (Derwent Abs. No. 84 196505).
Abstract of U.S. Pat. No. 4,479,941 (Derwent Abs. No. 84-287964).
Carl et al., Chem. Abst. 95-116014y (1981).
Cariello et al., Chem. Abst. 103-40927 (1985).
Castelhano et al., Chem. Abst. 110-7607h (1989).
Castelhano et al., Chem. Abst. 110-193339p (1989).

TRANSGLUTAMINASE INHIBITORS

This is a division of pending application Ser. No. 025,451, filed March 13, 1987, now U.S. Pat. No. 4,912,120, is a continuation-in-part of U.S. patent application Ser. No. 839,743, filed March 14, 1986, now abandoned.

BACKGROUND OF THE INVENTION

Transglutaminases are a family of enzymes that catalyze the calcium-dependent, post-translational modification of the γ-carboxamide group of peptide-bound glutamine residues. A key intermediate in the catalysis is a thioester acyl-enzyme complex. An ε-amino group of peptide-bound lysine is the acyl acceptor in protein crosslinking reactions:

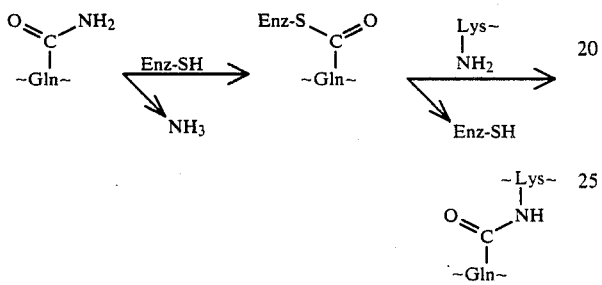

Alternatively, a free amine, such as putrescine, may act as an acyl acceptor resulting in the post-translational modification of proteins.

Transglutaminases have been implicated in a variety of disease states, including acne and cataracts. For example, regarding the acne state, changes in transglutaminase activity during comedogenesis have been demonstrated by DeYoung et al., in J. Investigative Dermatology, 82, 275 (1984). These investigators have demonstrated that in early acne lesions there is intense transglutaminase activity in the involved sebaceous follicles. In normal follicles no such activity is observed. Furthermore, Dalziel et al., in Br. J. Exp. Pathology 65, 107–115 (1984) have shown that the cornified cell envelope, a product of transglutaminase activity, produces chronic inflammation when intradermally injected. The cornified envelope is responsible for the rigid, resistant structure of differentiated squamous cells. The cornified envelopes in acne comedones play an important role in the resistant cohesive nature of these structures and in their inflammatory potential upon rupture. Therefore, a need exists for an inhibitor of transglutaminase effective in the suppression of cornified envelope formation.

With regard to psoriasis, Bernard et al. in British Journal of Dermatology, 114, 279 (1986) have demonstrated, by histochemical activity staining, the precocious distribution of transglutaminase activity down to the suprabasal layer of involved psoriatic epidermis. In addition, the distribution of involucrin, one of the major substrates for epidermal transglutaminase, matches the distribution of transglutaminase activity. Thus, in psoriasis, there is an apparent loss of integrated control of the independent pathways for terminal differentiation of keratinocytes, and the onset of involucrin and transglutaminase activity is favored. A need exists for effective transglutaminase inhibitors to modulate the elevated transglutaminase activity in psoriatic epidermis.

Hereditary cataractous rat lenses show significantly elevated transglutaminase activities (2.7 to 17.7 times higher specific activities for young and old animals respectively). See, Azari, P. et al., Current Eye Res, 1, 463 (1981).

Previously reported inhibitors of transglutaminase include alternate substrate inhibitors, covalent inactivators and active site directed inhibitors. The alternate substrate inhibitors include alkyl primary amines, such as monodansylcadaverine, and alternative acyl-donors, such as beta-phenyl propionylthiocholine. These inhibitors prevent protein crosslinking, but do not prevent post-translational modification of proteins. They suffer from the drawback that they are effective only in relatively high concentrations, i.e., at $10^{-3}$M or higher. The covalent inhibitors include alkyl isocyanates, such as $(CH_3)_2$—CH—$CH_2$—N=C=O, as titrants of active site cysteine residues, but these lack specificity for transglutaminases. An active site directed inhibitor is cystamine, which lacks specificity for transglutaminases and is effective only at concentrations of greater than $10^{-3}$M.

Accordingly, a need exists for specific and potent inactivators of transglutaminases, and particularly of epidermal transglutaminase.

SUMMARY OF THE INVENTION

One aspect of the invention relates to compounds having the formula:

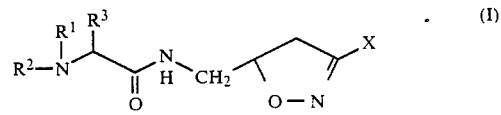

or an optical isomer thereof, or a pharmaceutically acceptable salt thereof, wherein:

$R^1$ and $R^2$, together with the nitrogen atom to which they are attached, together represent phthalimido; or $R^1$ and $R^3$ together form —$CH_2$—$CH_2$—$CH_2$— or $CH_2$—CHOH—$CH_2$; or $R^1$, $R^2$ and $R^3$ are defined as follows:

$R^1$ is hydrogen or methyl;

$R^2$ is selected from the group consisting of:
(1) hydrogen;
(2) alkyl;
(3) lower alkyl sulfonyl;
(4) aryl sulfonyl;
(5) aryl sulfonyl substituted with lower alkyl on the aryl moiety;
(6) 9-fluorenylmethyloxycarbonyl, succinyl or cinnamoyl;
(7) a radical of the formula:

wherein:

$R^9$ is hydrogen; alkyl of 1 to 4 carbon atoms; aryl; aryl substituted with up to 2 substituents where the substituents are independently halo, lower alkyl, alkoxy, nitro, trifluoromethyl, carboxyl, or alkoxycarbonyl; aralkyl; pyridinyl; furanyl; alkoxy; aralkoxy; aralkoxy substituted on the aryl radical with up to 2 substituents where the substituents are independently halo, lower alkyl, alkoxy, nitro, or trifluoromethyl; adamantyloxy; aralkylamino; or aralkyl substituted on the aryl radical with up to 2 substituents where the substituents are independently hydroxy, alkoxy or halo; and (8) a radical of the formula

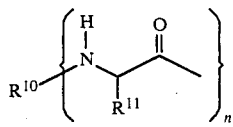
(III)

wherein:

n=0 or 1;

$R^{10}$ is independently hydrogen, alkyl or the radical defined by formula (II) above;

$R^{11}$ is selected from the group consisting of: hydrogen; lower alkyl; —$(CHR^{12})_m WR^{13}$ wherein m is 1 or 2, W is oxygen or sulfur and $R^{12}$ and $R^{13}$ are independently hydrogen or methyl; —$CH(CH_3)$—$OCH_2C_6H_5$; —$(CH_2)_k C(O)Y$ wherein k is 1 or 2 and Y is hydroxy, amino, alkoxy, or aralkoxy; —$(CH_2)_p NHCH(NHR^{14})NR^{15}$ wherein p is 2,3, or 4 and $R^{14}$ and $R^{15}$ are independently hydrogen or lower alkyl; —$(CH_2)_q NH_2$ wherein q is 2, 3, 4, or 5; —$(CH_2)_4 NHCOOC(CH_3)_3$; —$(CH_2)_2$-$CHOHCH_2NH_2$; a radical of formula

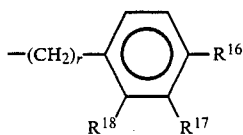

wherein r is 1 or 2 and $R^{16}$, $R^{17}$ and $R^{18}$ are independently hydrogen, hydroxy, halo, methoxy, lower alkyl, halo lower alkyl, amino, N-protected amino, guanidino, nitro, cyano, —COOH, —$CONH_2$, —$COOR'''$ where $R'''$ is lower alkyl or —$OR^*$ where $R^*$ is an O-protecting group; and a radical chosen from

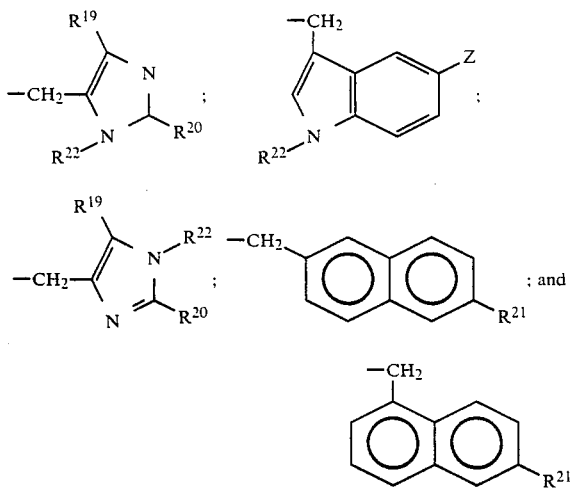

wherein $R^{19}$ and $R^{20}$ are independently hydrogen, lower alkyl, halo or trifluoromethyl alkyl; $R^{21}$ is hydrogen, hydroxy or methoxy; and Z is hydrogen, hydroxy, or —$OR^*$ where $R^*$ is an O-protecting group; $R^{22}$ is hydrogen or an N-protecting group for imidazole or indole functionalities;

$R^3$ is independently selected from the group recited for $R^{11}$ above;

X is selected from the group consisting of: halo; —OR, —SR, —S(O)R, —$S(O_2)R$, —$S(O)_2NH_2$ or —$S(O)_2NHR$ wherein R is lower alkyl mono-, di- or trifluoro alkyl of 2 or 3 carbon atoms, aryl, or optionally substituted aryl; —NR'R'' wherein R' and R'' are independently hydrogen, lower alkyl, or aryl; and

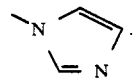

A second aspect of the invention relates to active intermediates in the synthesis of the compound of Formula (I).

A third aspect of the invention is a method for treating acne or cataracts in mammals, and most particularly in humans, wherein said method comprises administering a therapeutically effective amount of the compound of Formula I to a subject in need thereof.

A fourth aspect of the invention is a method for treating psoriasis in humans wherein said method comprises administering a therapeutically effective amount of the compound of Formula (I).

A fifth aspect of the invention is a pharmaceutical composition which comprises a compound of Formula (I) and a pharmaceutically acceptable excipient.

A sixth aspect of the invention is the processes for preparing a compound of Formula (I).

DETAILED DESCRIPTION AND PREFERRED EMBODIMENTS

Definitions

For the purposes of this invention, the following terms are to be understood to have the meanings set forth below.

"Alkyl" means a branched or unbranched, saturated aliphatic hydrocarbon radical, having the number of carbon atoms specified, or if no number is specified, having up to 8 carbon atoms. The prefix "alk-" is also indicative of a radical having up to 8 carbon atoms in the alkyl portion of that radical, unless otherwise specified. Examples of alkyl radicals include methyl, ethyl, n-propyl, isopropyl, n-butyl, tert-butyl and the like. The terms "lower alkyl" and "alkyl of 1 to 4 carbon atoms" are synonymous and used interchangeably.

"Alkoxy" means an alkyl radical of up to 8 carbon atoms unless otherwise specified, that is attached to an oxygen radical, which is in turn attached to the structure provided. Examples are, methoxy, ethoxy, propoxy, n-butoxy, isobutoxy, tert-butoxy, n-pentoxy, n-hexoxy, n-heptoxy, n-octoxy, and the like.

"Alkoxycarbonyl" means an alkoxy radical (as defined above) attached to a carbonyl radical, which in turn is attached to the structure provided. Examples are methoxycarbonyl, ethoxycarbonyl, propoxycarbonyl, n-butoxycarbonyl, isobutoxycarbonyl, tert-butoxycarbonyl, n-pentoxycarbonyl, n-hexoxycarbonyl, n-heptoxycarbonyl, n-octoxycarbonyl, and the like.

"Aralkoxy" means an aralkyl radical (as defined below) that is attached to an oxygen radical, which is in turn attached to the structure provided. Examples are benzyloxy, naphthylmethoxy, and the like.

"Aralkyl" means an aryl group (as defined below) attached to a lower alkyl radical, which is in turn attached to the structure provided. Examples are, benzyl, naphthylmethyl, and the like.

"Aryl" means phenyl, 1-naphthyl or 2-naphthyl.

"Boc" means t-butyloxycarbonyl.

"BOC-ON" is [2-(tertbutoxycarbonyloxyimino)-2-phenylacetylnitrile].

"Cbz" means benzyloxycarbonyl.

"DCC" means N,N'-dicyclohexylcarbodiimide.

"DMAP" means 4-dimethylaminopyridine.

"EDCI" means 1-(3-dimethylaminopropyl)-3-ethylcarbodiimide.

"Fmoc" means 9-fluorenylmethyloxycarbonyl.

"Halo" means bromo, chloro, fluoro or iodo.

"N-Protecting groups" can be considered to fall within five classes: N-acyl, N-alkoxycarbonyl, N-arylmethoxycarbonyl, N-arylmethyl, and N-arylsulfonyl protecting groups. An N-acyl protecting group is a lower alkyl carbonyl radical, a trifluoroacetyl radical. An N-alkoxycarbonyl protecting group is a lower alkoxycarbonyl radical. An N-arylmethoxycarbonyl protecting group is a 9-fluoroenemethoxycarbonyl radical (Fmoc); or benzyloxycarbonyl radical which can optionally be substituted on the aromatic ring with p-methoxy, p-nitro, p-chloro, or o-chloro. An N-arylmethyl protecting group is a benzyl radical, which can optionally be substituted on the aromatic ring with p-methoxy, p-nitro, or p-chloro. An N-arylsulfonyl protecting group is a phenylsulfonyl radical, which can optionally be substituted on the aromatic ring with p-methyl ("tosyl") or p-methoxy.

"N-Protecting groups" for imidazole functionalities on histidine amino acid side chains are known in the art, and described in "The Peptides," Vol. 3, pp. 70-80, and "Chemistry of the Amino Acids," Vol. 2, pp. 1060-1068, as cited earlier. These include the benzyl, triphenylmethyl (trityl), 2,4-dinitrophenyl, p-toluenesulfonyl, benzoyl, and Cbz N-protecting groups.

"N-Protecting groups" for indole functionalities on tryptophan amino acid side chains are known in the art and described in "The Peptides," Vol. 3, pp. 82–84, as cited earlier. These include the formyl and Cbz N-protecting groups.

"O-Protecting groups" for hydroxy functionalities on amino acid side chains are known in the art and described in "The Peptides," Vol. 3, pp. 169-201, and "Chemistry of the Amino Acids," Vol. 2, pp. 1050-1056, as cited earlier. For aromatic hydroxy functionalities, suitable O-protecting groups include the benzyl, acetyl, tert-butyl, methyl, Cbz, and tosyl groups.

"N-Protecting groups" for amine functionalities are well known in the art, and include Boc, Cbz, Fmoc, phthaloyl, benzoyl, mesyl, tosyl, and the like.

"Optional" or "optionally" means that the subsequently described event or circumstance may or may not occur, and that the description includes instances where said event or circumstance occurs and instances in which it does not. For example, "optionally substituted phenyl" means that the phenyl may or may not be substituted and that the description includes both unsubstituted phenyl and phenyl wherein there is substitution; "optionally followed by converting the free base to the acid addition salt" means that said conversion may or may not be carried out in order for the process described to fall within the invention, and the invention includes those processes wherein the free base is converted to the acid addition salt and those processes in which it is not.

"Optionally substituted aryl" means aryl, aryl containing 1 to 5 fluoro substituents; or aryl containing 1 to 3 substituents, where the substituents are independently selected from the group consisting of alkoxy, alkyl, nitro, trifluoromethyl, —COOH, —COOR''' wherein R''' is lower alkyl or —CON$_2$H.

"Pharmaceutically acceptable acid addition salt" refers to those salts which retain the biological effectiveness and properties of the free bases and which are not biologically or otherwise undesirable, formed with inorganic acids such as hydrochloric acid, hydrobromic acid, sulfuric acid, nitric acid, phosphoric acid and the like, and organic acids such as acetic acid, propionic acid, glycolic acid, pyruvic acid, oxalic acid, malic acid, malonic acid, succinic acid, maleic acid, fumaric acid, tartaric acid, citric acid, benzoic acid, cinnamic acid, mandelic acid, methanesulfonic acid, ethanesulfonic acid, p-toluenesulfonic acid, salicylic acid and the like.

"Phthalimido" in the claims and this disclosure means that $R^1$, $R^2$ and the nitrogen to which they are attached together form the structure:

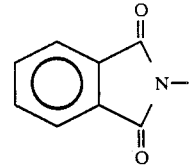

The compounds of this invention are named as 3,5 substituted 4,5-dihydroisoxazoles, where the oxygen atom of the isoxazole ring is numbered as 1, and the nitrogen atom of that ring is numbered as 2. The radical that is substituted at the 5 position is named in the order of: amino protecting group (if any); amino acid residue; "amido," representing the nitrogen linkage between the carboxy terminus of the amino acid residue and the remainder of the molecule; and finally, the radical bonded to the dihydroisozazole ring. For example, the name 5-[benzyloxycarbonyl-(L-phenylalanine)-amidomethyl]-3-chloro-4,5-dihydroisoxazole represents the compound represented by the structure:

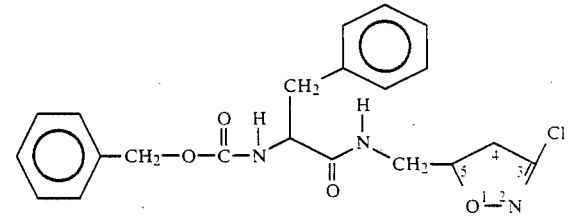

Preferred Embodiments

Preferred embodiments are compounds of Formula (I) wherein $R^1$ is hydrogen; $R^2$ is a radical of Formula II as set forth in the Summary above, wherein $R^9$ is selected from: pyridinyl; aryl; aryl substituted with up to 2 substituents where the substituents are independently halo, lower alkyl, alkoxy, nitro, trifluoromethyl, carboxyl or alkoxycarbonyl; aralkyl; alkoxy; aralkoxy; and aralkoxy substituted on the aryl radical with up to 2 substituents independently selected from halo, lower alkyl, alkoxy, nitro, and trifluoromethyl; adamantyloxy; aralkylamino; aralkyl substituted on the aryl radical with up to 2 substituents where the substituents are independently hydroxy, alkoxy, or halo; or $R^2$ is a radical of Formula III as set forth above, wherein $R^{10}$ is commensurate with the scope of Formula II as set forth above in this paragraph; or $R^1$ and $R^2$ together with the nitrogen to which they are attached, represent phthalimido; and X is halo, —OR, —SR, —S(O)R, —S(O)$_2$R, —S(O)$_2$NH$_2$, or —S(O)$_2$NHR wherein R is aryl or optionally substituted aryl.

More preferred are those preferred compounds as defined in the immediately preceding paragraph, but wherein $R^9$ is alkoxy; aralkoxy; aralkoxy substituted on the aryl radical with up to 2 substituents independently selected from halo, lower alkyl, alkoxy, nitro, and trifluoromethyl; adamantyloxy; aralkylamino; aralkyl; aralkyl substituted on the aryl radical with up to 2 substituents where the substituents are independently hydroxy, alkoxy, or halo; and wherein $R^{10}$ is commensurate with the scope of Formula II as defined in this paragraph (in accordance with the more preferred definition of $R^9$ as set forth in this sentence); and X is halo.

Most preferred are those more preferred compounds as defined in the immediately preceding paragraph, but $R^9$ is aralkoxy; aralkoxy substituted on the aryl ring with a substituent selected from halo or alkoxy; aralkyl; aralkyl substituted on the aryl radical with up to 2 substituents where the substituents are independently hydroxy, alkoxy, or halo; and wherein $R^{10}$ is commensurate with the scope of Formula II as defined in this paragraph (in accordance with the most preferred definition of $R^9$ as set forth in this sentence); and X is chloro or bromo.

Generally, 5-S stereochemistry is preferred.

Specifically preferred compounds are set forth
in the following table and named below:

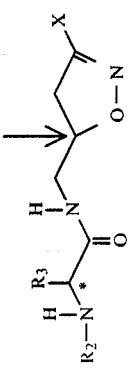

| R² | R³ | X | Chirality at* | Chirality at C-5 (of isoxazole ring) | Comments |
|---|---|---|---|---|---|
| C₆H₅—CH₂—O—CO— | —CH₂—C₆H₅ | Cl | L isomer | Chiral (R or S) | less polar diastereomer |
| C₆H₅—CH₂—O—CO— | —CH₂—C₆H₅ | Cl | L isomer | Chiral (R or S) | more polar diastereomer |
| C₆H₅—CH₂—O—CO— | —CH₂—C₆H₅ | Br | L isomer | Racemic | mixture of diastereomers |
| C₆H₅—CH₂—O—CO— | —CH₂—C₆H₅ | Br | L isomer | Chiral (R or S) | less polar diastereomer |
| C₆H₅—CH₂—O—CO— | —CH₂—C₆H₅ | Br | L isomer | Chiral (R or S) | more polar diastereomer |
| C₆H₅—CH₂—O—CO— | CH₂—C₆H₄-(p)OH | Br | L isomer | Racemic | mixture of diastereomers |
| C₆H₅—CH₂—O—CO— | CH₂—C₆H₄-(o)OH | Br | L isomer | Racemic | mixture of diastereomers |
| C₆H₅—CH₂—O—CO— | —CH₂—C₁₀H₇ | Cl | D isomer | Chiral (R or S) | less polar diastereomer |
| C₆H₅—CH₂—O—CO— | —CH₂—C₁₀H₇ | Cl | D isomer | Chiral (R or S) | more polar diastereomer |
| C₆H₅—CH₂—O—CO— | —CH₂—C₆H₄-(p)Cl | Cl | D isomer | Chiral (R or S) | less polar diastereomer |
| C₆H₅—CH₂—O—CO— | —CH₂—C₆H₄-(p)Cl | Cl | D isomer | Chiral (R or S) | more polar diastereomer |
| C₆H₅—CH₂—O—CO— | —CH₂—C₆H₅ | Br | L isomer | Racemic | mixture of diastereomers |
| (CH₃)₃C—O—CO— | —CH₂—COOH | Br | L isomer | Racemic | mixture of diastereomers |
| C₆H₅—CH₂—O—CO— | —CH₂—CH₂—COOH | Br | L isomer | Racemic | mixture of diastereomers |
| C₆H₅—CH₂—O—CO— | —(CH₂)₄—NH—CO—O—C(CH₃)₃ | Br | L isomer | Racemic | mixture of diastereomers |
| C₆H₅—CH₂—O—CO— | —CH₂—O—CH₂—C₆H₅ | Br | L isomer | Racemic | mixture of diastereomers |
| C₆H₅—CH₂—O—CO— | —CH₂—C₁₀H₇ | Br | L isomer | Racemic | mixture of diastereomers |
| CH₃—CO— | —H | Br | Achiral | Racemic | Racemic |
| C₆H₅—CH₂—O—CO— | —CH(CH₃)—CH₂—CH₃ | Br | L isomer | Racemic | mixture of diastereomers |
| C₆H₅—CH₂—O—CO— | —CH₂—C₆H₅ | Br | L isomer | Racemic | mixture of diastereomers |
| C₁₃H₉—CH₂—O—CO— | —CH(CH₃)—O—CH₂—C₆H₅ | Br | L isomer | Racemic | mixture of diastereomers |
| (CH₃)₃C—O—CO | —CH(OH)—CH₃ | Br | L isomer | Racemic | mixture of diastereomers |
| C₆H₅—CH₂—O—CO— | —CH₃ | Br | L isomer | Racemic | mixture of diastereomers |
| C₆H₅—CH₂—O—CO—NH—CH—CO— \| CH₂C₆H₅ | —CH₂C₆H₅ | Br | L isomer | Racemic | mixture of diastereomers |
| C₆H₅—CH₂—O—CO—NH—CH—CO— \| CH₃ | —CH₂C₆H₅ | Br | L isomer | Racemic | mixture of diastereomers |
| C₆H₅—CO— | —CH₂C₆H₅ | Br | L isomer | Racemic | mixture of diastereomers |
| C₆H₅CH₂—O—CO— | —CH₂—C₆H₅ | Br | D isomer | Racemic | mixture of diastereomers |
| C₆H₅—CH₂—CH₂—CO— | —CH₂—C₁₀H₇ | Br | L isomer | Racemic | mixture of diastereomers |
| C₆H₅—CH₂—CH₂—CO— | —CH₂C₆H₅ | Br | L isomer | racemic | mixture of diastereomers |
| phthalimido (with R¹) C₈H₄O₂ | —CH₂C₆H₅ | Cl | D, L isomer | Racemic | mixture of diastereomers |
| C₆H₅—CH₂—O—CO— | —CH₂—C₆H₄-(p)OH | Cl | L isomer | Racemic | mixture of diastereomers |
| C₆H₅—CH₂—O—CO— | —CH₂—C₆H₄-(p)OH | Br | L isomer | Racemic | mixture of diastereomers |
| C₆H₅—CH₂—O—CO— | —CH₂—C₆H₄-(o)OH | Br | L isomer | Racemic | mixture of diastereomers |
| C₆H₅—CH₂—O—CO— | —CH₂—C₆H₄-(m)OH | Br | L isomer | Racemic | mixture of diastereomers |
| C₆H₅—CH₂—O—CO— | —CH₂—C₆H₄-(m)OH | Cl | L isomer | Racemic | mixture of diastereomers |

-continued

Specifically preferred compounds are set forth in the following table and named below:

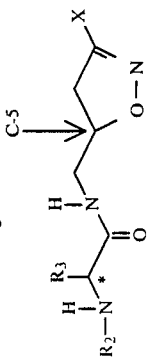

| R² | R³ | X | Chirality at* | Chirality at C-5 (of isoxazole ring) | Comments |
|---|---|---|---|---|---|
| C₆H₅—CH₂—O—CO— | —CH₂—C₆H₄-(3-OMe) | Cl | L-isomer | Racemic | mixture of diastereomers |
| C₆H₅—CH₂—O—CO— | —CH₂—C₆H₄-(3-OMe) | Br | L-isomer | Racemic | mixture of diastereomers |
| C₆H₅—CH₂—O—CO— | —CH₂—C₆H₄-(4-OMe) | Cl | L-isomer | Racemic | mixture of diastereomers |
| C₆H₅—CH₂—O—CO— | —CH₂—C₆H₄-(4-OMe) | Br | L-isomer | Racemic | mixture of diastereomers |
| C₆H₅—CH₂—O—CO— | —CH₂-indolyl | Cl | L-isomer | Racemic | mixture of diastereomers |
| C₆H₅—CH₂—O—CO— | —CH₂-indolyl | Br | L-isomer | Racemic | mixture of diastereomers |
| C₆H₅—CH₂—O—CO— | —CH₂-(5-OH)indolyl | Cl | L-isomer | Racemic | mixture of diastereomers |
| C₆H₅—CH₂—O—CO— | —CH₂-(5-OH)indolyl | Br | L-isomer | Racemic | mixture of diastereomers |
| C₆H₅—CH₂—O—CO— | —CH₂— (imidazolyl NH) | Br | L-isomer | Racemic | mixture |
| C₆H₅—CH₂—O—CO— | —CH₂— (imidazolyl N—CO—C₆H₅) | Br | L-isomer | Racemic | mixture |
| (4-CH₃)C₆H₄—SO₂— | —H | Br | Achiral | Racemic | racemic |
| C₆H₅—CH₂—NH—CO— | —CH₂—C₆H₅ | Br | L-isomer | Racemic | mixture |
| C₆H₅—CH₂—O—CO— | —CH₂—CH(OH)—CH₂— ((together with R₁)) | Br | L-isomer | Racemic | mixture |
| C₆H₅—CH₂—O—CO— | —CH₂—C₆H₄-(4-OMe) | Br | L-isomer | Racemic | mixture |
| C₆H₅—CH₂—O—CO— | —CH₂-indolyl-(5-O—CO—O—CH₂C₆H₅) | Br | L-isomer | Racemic | mixture |
| C₆H₅—CH₂—O—CO— | —CH₂—C₆H₃-(3,4-di-(O—CO—CH₂C₆H₅) | Br | D,L-isomers | Racemic | mixture |
| C₆H₅—CH₂—O—CO— | —CH₂—C₆H₃-(3,4-di(OH)) | Br | D,L-isomers | Racemic | mixture |
| C₆H₅—CH₂—O—CO— | —CH₂—C₆H₄-(4-F) | Br | L-isomer | Racemic | mixture |
| (CH₃)₃C—O—CO—NH—CH—CO—<br>\|<br>CH₂C₆H₅ | —CH₂—C₆H₄-(4-OH) | Br | L-isomer | Racemic | mixture |
| C₆H₅—CH₂—O—CO— | —CH₂—C₆H₄-(4-NH—CO—O—CH₂—C₆H₅) | Br | L-isomer | Racemic | mixture |
| C₆H₅—CH₂—O—CO— | —CH₂-indolyl-1((N)—CHO)) | Br | L-isomer | Racemic | mixture |
| C₆H₅—CH₂—O—CO— | —CH₂—C₆H₄-(4-NH₂) | Br | L-isomer | Racemic | mixture |
| H₂N—CH—CO—<br>\|<br>CH₂C₆H₅ | —CH₂—C₆H₄-(4-OH) | Br | L-isomer | Racemic | mixture |

-continued

Specifically preferred compounds are set forth in the following table and named below:

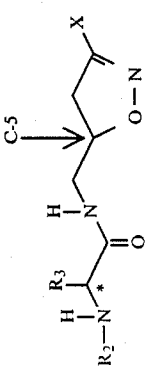

| R² | R³ | X | Chirality at* | Chirality at C-5 (of isoxazole ring) | Comments |
|---|---|---|---|---|---|
| $C_6H_5$—$CH_2$—O—CO— | —$CH_2$—S—$CH_2$—$C_6H_5$ | Br | L-isomer | Racemic | mixture |
| $C_6H_5$—$CH_2$—O—CO— | —$CH_2C_6H_3$(3-OMe) (4-O—CO—O—$CH_2C_6H_5$) | Br | L-isomer | Racemic | mixture |
| $C_6H_5$—$CH_2$—O—CO— | —$CH_2$—$C_6H_3$(3-OMe)(4-OH) | Br | L-isomer | Racemic | mixture |
| $C_6H_5$—$CH_2$—O—CO— | —$CH_2$—$C_6H_4$-(4-I) | Br | D,L-mixture | Racemic | mixture |
| 2-((6-MeO)—$C_{10}H_6$)—CH—CO—<br>$\|$<br>$CH_3$ | —$CH_2$—$C_6H_4$-(4-OH) | Br | L-isomer | Chiral (S) | more polar |
| $C_6H_5$—$CH_2$—O—CO— | —$CH_2$—$CH_2$—COOH | Cl | L-isomer | Racemic | mixture |
| (4-MeO)$C_6H_4$—$CH_2$—O—CO— | —$CH_2$—$C_6H_4$-(4-OH) | Cl | L-isomer | Chiral (S) | more polar |
| 2-((6-MeO)—$C_{10}H_6$)—CH—CO—<br>$\|$<br>$CH_3$ | —$CH_2$—$C_6H_4$-(4-OH) | Cl | L-isomer | Chiral (S) | more polar |
| 2-($C_{10}H_7$)—$CH_2$—CO— | —$CH_2$—$C_6H_4$-(4-OH) | Cl | L-isomer | Chiral (S) | more polar |
| 1-($C_{10}H_7$)—$CH_2$—CO— | —$CH_2$—$C_6H_4$-(4-OH) | Cl | L-isomer | Chiral (S) | more polar |
| $(CH_3)_2CH$—$CH_2$—$CH_2$—CO— | —$CH_2$—$C_6H_5$ | Br | L-isomer | Racemic | mixture |
| HOOC—$CH_2$—$CH_2$—CO— | —$CH_2$—$C_6H_5$ | Br | L-isomer | Racemic | mixture |
| $C_6H_5CH_2$—O—CO—NH—CH—CO—<br>$\|$<br>$CH_3$—CH—OH | —$CH_2$—$C_6H_5$ | Br | L-isomer | Racemic | mixture |
| $C_6H_5$—CH=CH—CO— | —$CH_2$—$C_6H_5$ | Br | L-isomer | Racemic | mixture |
| 2-((6-MeO)$C_{10}H_6$)—CH—CO—<br>$\|$<br>$CH_3$ | —$CH_2$—$C_6H_5$ | Br | L-isomer | Racemic | mixture |
| 2-((6-MeO)$C_{10}H_6$)—CH—CO—<br>$\|$<br>$CH_3$ | —$CH_2$—$C_6H_5$ | Br | L-isomer | Chiral (R) | less polar |
| 2-((6-MeO)$C_{10}H_6$)—CH—CO—<br>$\|$<br>$CH_3$ | —$CH_2$—$C_6H_5$ | Br | L-isomer | Chiral (S) | more polar |

Specifically preferred compounds are set forth in the following table and named below:

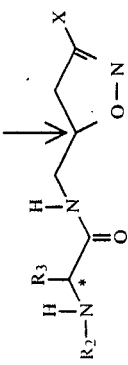

| R² | R³ | X | Chirality at* | Chirality at C-5 (of isoxazole ring) | Comments |
|---|---|---|---|---|---|
| C₁₀H₁₅—O—CO— (C₁₀H₁₅ = adamantyl) | —CH₂—C₆H₅ | Br | L-isomer | Racemic | mixture |
| (2-Cl)C₆H₄—CH₂—O—CO— | —CH₂—C₆H₅ | Br | L-isomer | Racemic | mixture |
| (4-MeO)C₆H₄—CH₂—O—CO— | —CH₂—C₆H₅ | Br | L-isomer | Racemic | mixture |
| (4-MeO)C₆H₄—CH₂—O—CO— | —CH₂—C₆H₅ | Br | L-isomer | Chiral (R) | less polar |
| (4-MeO)C₆H₄—CH₂—O—CO— | —CH₂—C₆H₅ | Br | L-isomer | Chiral (S) | more polar |
| C₆H₅—CH₂—O—CO— | —(CH₂)—NH₂ (oxalate salt) | Br | L-isomer | Racemic | mixture |
| H₂N—CH₂—CO— (Oxalate salt) | —CH₂—C₆H₅ | Br | L-isomer | Racemic | mixture |

5-(N-benzyloxycarbonyl-L-phenylalaninamidomethyl)-3-chloro-4,5-dihydroisoxazole;
5-(N-benzyloxycarbonyl-L-phenylalaninamidomethyl)-3-bromo-4,5-dihydroisoxazole;
5-(N-benzyloxycarbonyl-L-para-tyrosinamidomethyl)-3-bromo-4,5-dihydroisoxazole;
5-(N-benzyloxycarbonyl-L-ortho-tyrosinamidomethyl)-3-bromo-4,5-dihydroisoxazole;
5-(N-benzyloxycarbonyl-D-naphthylalaninamidomethyl)-3-chloro-4,5-dihydroisoxazole;
5-(N-benzyloxycarbonyl-D-para-chloro-phenylalaninamidomethyl)-3-chloro-4,5-dihydroisoxazole;
5-(N-tert-butoxycarbonyl-L-phenylalaninamidomethyl)-3-bromo-4,5-dihydroisoxazole;
5-(N-benzyloxycarbonyl-L-aspartic acid-$\alpha$-amidomethyl)-3-bromo-4,5-dihydroisoxazole;
5-(N-benzyloxycarbonyl-L-glutamic acid-$\alpha$-amidomethyl)-3-bromo-4,5-dihydroisoxazole;
5-(N-benzyloxycarbonyl-N-$\epsilon$-tert-butoxycarbonyl-L-lysine-amidomethyl)-3-bromo-4,5-dihydroisoxazole;
5-(N-benzyloxycarbonyl-$\beta$-benzyl-L-aspartic acid amidomethyl)-3-bromo-4,5-dihydroisoxazole;
5-(N-acetyl-L-naphthylalaninamidomethyl)-3-bromo-4,5-dihydroisoxazole;
5-(N-benzyloxycarbonyl-glycinamidomethyl)-3-bromo-4,5-dihydroisoxazole;
5-(N-benzyloxycarbonyl-L-isoleucinamidomethyl)-3-bromo-4,5-dihydroisoxazole;
5-(N-[9-fluorenylmethyloxycarbonyl]-L-phenylalaninamidomethyl)-3-bromo-4,5-dihydroisoxazole;
5-(N-tert-butoxycarbonyl-O-benzyl-L-threoninamidomethyl)-3-bromo-4,5-dihydroisoxazole;
5-(N-benzyloxycarbonyl-L-threoninamidomethyl)-3-bromo-4,5-dihydroisoxazole;
5-(N-benzyloxycarbonyl-L-phenylalaninyl-L-alaninamidomethyl)-3-bromo-4,5-dihydroisoxazole;
5-(N-benzyloxycarbonyl-L-alanyl-L-phenylalaninamidomethyl)-3-bromo-4,5-dihydroisoxazole;
5-(N-benzoyl-L-phenylalaninamidomethyl)-3-bromo-4,5-dihydroisoxazole;
5-(N-benzyloxycarbonyl-D-phenylalaninamidomethyl)-3-bromo-4,5-dihydroisoxazole;
5-(N-benzyloxycarbonyl-L-naphthylmethyl-glycinamidomethyl)-3-bromo-4,5-dihydroisoxazole;
5-(N-benzyloxycarbonyl-L-$\gamma$-glutamine amidomethyl)-3-bromo-4,5-dihydroisoxazole;
5-(N-phthaloyl-L-phenylalaninamidomethyl)-3-bromo-4,5-dihydroisoxazole;
5-(N-benzyloxycarbonyl-D,L-meta-tyrosinamidomethyl)-3-bromo-4,5-dihydroisoxazole;
5-(N-benzyloxycarbonyl-L-para-tyrosinamidomethyl)-3-chloro-4,5-dihydroisoxazole;
5-(N-benzyloxycarbonyl-L-ortho-tyrosinamidomethyl)-3-chloro-4,5-dihydroisoxazole;
5-(N-benzyloxycarbonyl-L-meta-tyrosinamidomethyl)-3-bromo-4,5-dihydroisoxazole;
5-(N-benzyloxycarbonyl-L-meta-tyrosinamidomethyl)-3-chloro-4,5-dihydroisoxazole;
5-(N-benzyloxycarbonyl-L-3-methoxy-phenylalaninamidomethyl)-3-bromo-4,5-dihydroisoxazole;
5-(N-benzyloxycarbonyl-L-3-methoxy-phenylalaninamidomethyl)-3-chloro-4,5-dihydroisoxazole;
5-(N-benzyloxycarbonyl-L-4-methoxy-phenylalaninamidomethyl)-3-bromo-4,5-dihydroisoxazole;
5-(N-benzyloxycarbonyl-L-4-methoxy-phenylalaninamidomethyl)-3-chloro-4,5-dihydroisoxazole;
5-(N-benzyloxycarbonyl-L-tryptophanamidomethyl)-3-bromo-4,5-dihydroisoxazole;
5-(N-benzyloxycarbonyl-L-tryptophanamidomethyl)-3-chloro-4,5-dihydroisoxazole;
5-(N-benzyloxycarbonyl-L-5-hydroxytrypto-phanamidomethyl)-3-bromo-4,5-dihydroisoxazole;
5-(N-benzyloxycarbonyl-L-5-hydroxytrypto-phanamidomethyl)-3-chloro-4,5-dihydroisoxazole;
5-(N-benzyloxycarbonyl-L-histidinamidomethyl-3-bromo-4,5-dihydroisoxazole;
5-(N-im-benzoyl-N-$\alpha$-benzyloxycarbonyl-L-histidinamidomethyl)-3-bromo-4,5-dihydroisoxazole;
5-(N-toluenesulfonyl glycinamidomethyl)-3-bromo-4,5-dihydroisoxazole;
5-[N-(4-benzylcarbamoyl-L-phenylalaninamidomethyl]-3-bromo-4,5-dihydroisoxazole;
5-[N-benzyloxycarbonyl-4-(R)-hydroxy-L-prolinamidomethyl]-3-bromo-4,5-dihydroisoxazole;
5-(N-benzyloxycarbonyl-L-para-methoxy-L-phenylalaninamidomethyl)-3-bromo-4,5-dihydroisoxazole;
5-($N^\alpha$,O-dibenzyloxycarbonyl-L-5-hydroxytrypto-phanamidomethyl)-3-bromo-4,5-dihydroisoxazole;
5-[N,O,O-tribenzyloxycarbonyl-($\pm$)-3,4-dihydroxy-phenylalaninamidomethyl]-3-bromo-4,5-dihydroisoxazole;
5-[N-benzyloxycarbonyl-($\pm$)-3,4-dihydroxy-phenylalaninamidomethyl]-3-bromo-4,5-dihydroisoxazole;
5-[N-benzyloxycarbonyl-($\pm$)-para-fluoro-phenylalaninamidomethyl]-3-bromo-4,5-dihydroisoxazole;
5-(N-tert-butoxycarbonyl-L-phenylalanyl-L-tyrosinamidomethyl)-3-bromo-4,5-dihydroisoxazole;
5-($N^\alpha$,N-dibenzyloxycarbonyl-L-4-amino-phenylalaninamidomethyl)-3-bromo-4,5-dihydroisoxazole;
5-($N^\alpha$-benzyloxycarbonyl-$N^{im}$-formyl-L-trypto-phanamidomethyl)-3-bromo-4,5-dihydroisoxazole;
5-(N-benzyloxycarbonyl-L-para-amino-phenylalaninamidomethyl)-3-bromo-4,5-dihydroisoxazole;
5-(L-phenylalanyl-L-tyrosinamidomethyl)-3-bromo-4,5-dihydroisoxazole-para-toluene-sulfonic acid;
5-(N-benzyloxycarbonyl-S-benzyl-L-cysteinamidomethyl)-3-bromo-4,5-dihydroisoxazole;
5-(N-benzyloxycarbonyl-L-methioninamidomethyl)-3-bromo-4,5-dihydroisoxazole;
5-(N-benzyloxycarbonyl-O-acetyl-L-tyrosinamidomethyl)-5-(S)-3-bromo-4,5-dihydroisoxazole;
5-(N,O-dibenzyloxycarbonyl-3-methoxy-L-tyrosinamidomethyl)-3-bromo-4,5-dihydroisoxazole;
5-(N-benzyloxycarbonyl-3-methoxy-L-tyrosinamidomethyl)-3-bromo-4,5-dihydroisoxazole;
5-(N-benzyloxycarbonyl-($\pm$)-para-iodo-phenylalaninamidomethyl)-3-bromo-4,5-dihydroisoxazole;
5-[N-2-(S)-(6-methoxy-2-naphthyl)-propionyl-L-tyrosinamidomethyl]-5-(S)-3-bromo-4,5-dihydroisoxazole;
5-(N-$\alpha$-benzyloxycarbonyl-L-glutamic acid-$\alpha$-amidomethyl)-3-chloro-4,5-dihydroisoxazole;

5-(N-para-methoxybenzyloxycarbonyl-L-tyrosinamidomethyl)-5-(S)-3-chloro-4,5-dihydroisoxazole;

5-[N-[2-(S)-(6-methoxy-2-naphthyl)-propionyl]-L-tyrosinamidomethyl]-5-(S)-3-chloro-4,5-dihydroisoxazole;

5-[N-(2-naphthyl-acetyl)-L-tyrosinamidomethyl-5-(S)-3-chloro-4,5-dihydroisoxazole;

5-[N-(1-Naphthyl-acetyl)-L-tyrosinamidomethyl]-5-(S)-3-chloro-4,5-dihydroisoxazole;

5-(N-isobutyloxycarbonyl-L-phenylalaninamidomethyl)-3-bromo-4,5-dihydroisoxazole;

5-(N-succinyl-L-phenylalaninamidomethyl)-3-bromo-4,5-dihydroisoxazole;

5-(N-benzyloxycarbonyl-L-threonyl-L-phenylalaninamidomethyl)-3-bromo-4,5-dihydroisoxazole;

5-[N-cinnamoyl-L-phenylalaninamidomethyl)-3-bromo-4,5-dihydroisoxazole;

5-[N-(2(S)-6-methoxy-2-naphthylpropionyl)-L-phenylalaninamidomethyl]-3-bromo-4,5-dihydroisoxazole;

5-[N-(2(S)-6-methoxy-2-naphthylpropionyl)-L-phenylalaninamidomethyl]-5-(R)-3-bromo-4,5-dihydroisoxazole;

5-[N-(2-(S)-6-methoxy-2-naphthylpropionyl)-L-phenylalaninamidomethyl]-5-(S)-3-bromo-4,5-dihydroisoxazole;

5-(N-adamantyloxycarbonyl-L-phenylalaninamidomethyl)-3-bromo-4,5-dihydroisoxazole;

5-(N-2-chlorobenzyloxycarbonyl-L-phenylalaninamidomethyl)-3-bromo-4,5-dihydroisoxazole;

5-[N-(4-methoxybenzyloxycarbonyl)-L-phenylalaninamidomethyl]-3-bromo-4,5-dihydroisoxazole;

5-[N-(4-methoxybenzyloxycarbonyl)-L-phenylalaninamidomethyl]-5-(R)-3-bromo-4,5-dihydroisoxazole;

5-[N-(4-methoxybenzyloxycarbonyl)-L-phenylalaninamidomethyl]-5-(S)-3-bromo-4,5-dihydroisoxazole;

5-(N-tertbutoxycarbonyl-glycyl-L-phenylalaninamidomethyl)-3-bromo-4,5-dihydroisoxazole;

5-(N-α-benzyloxycarbonyl-L-lysinamidomethyl)-3-bromo-4,5-dihydroisoxazole oxalic acid;

5-(glycyl-L-phenylalaninamidomethyl)-3-bromo-4,5-dihydroisoxazole oxalate salt;

5-(N-(6-methoxynaphthylacetyl)-L-phenylalaninamidomethyl)-3-chloro-4,5-dihydroisoxazole; and 5-(N-(6-methoxynaphthylacetyl)-L-tyrosinamidomethyl)-3-chloro-4,5-dihydroisoxazole.

In particular, the most polar diastereomer of 5-(N-benzyloxycarbonyl-L-para-tyrosinamidomethyl)-3-chloro-4,5-dihydroisoxazole is presently the most preferred compound. It has 5-S stereochemistry (noted by the insertion of "-5-(S)-" before "-3-chloro"), meaning that at C-5 of the isoxazole ring the (S) orientation is preferred.

Utility and Administration

The compounds of Formula (I) are useful for treating mammals, particularly humans, which have a disease state characterized by elevated transglutaminase activity. Such disease states are exemplified by acne, psoriasis and cataracts. The compounds of Formula (I) are particularly valuable because they are more potent and more selective than other known transglutaminase inhibitors. Further, the compounds of Formula (I) irreversibly inhibit transglutaminase.

The transglutaminase inhibitory activity of the compounds of this invention can be determined in vitro by accepted procedures described in the literature. See, e.g., DeYoung and Ballaron, *J. of Invest. Dermatology*, 79, (1982).

To determine the utility of the compounds of Formula (I) for treating acne in mammals, one can use the procedures described by DeYoung, et al. Another model examined is the Mexican hairless beagle dog, a procedure for which is set forth in Example 10. Many of these animals demonstrate a spontaneous acne-like condition with lesions similar to human open and closed comedones (Bedord, et al., *J. Invest. Dermatology*, 77, 1981).

To determine the utility of the compounds of Formula (I) for treating psoriasis in humans, the procedure of Example 13 can be followed.

The compounds of this invention are administered to a mammal in need thereof in a therapeutically effective dose. Such a dose is an amount sufficient to treat the disease state, i.e. inhibit transglutaminase.

While the components of this invention may be administered in any acceptable mode, they are best administered topically in combination with a suitable pharmaceutical excipient. Such a combination will include a therapeutically effective amount of a compound of formula (I), e.g., about 0.01% to about 10% by weight, with the rest being excipient(s).

For the treatment of acne, the preferred manner of administration is topically using a convenient dosage form which can be readily applied to skin and will maintain the active compounds there until beneficial action can occur. For such topical administration, a pharmaceutically acceptable non-toxic formulation can take the form of semisolid, liquid, or solid, such as, for example, gels, creams, lotions, solutions, suspensions, ointments, powders, or the like. As an example, the active components may be formulated into a gel using ethanol, propylene glycol, propylene carbonate, polyethylene glycols, diisopropyl adipate, glycerol, water, etc., with appropriate gelling agents, such as Carbomers, Klucels, etc. If desired, the formulation may also contain minor amounts of non-toxic auxiliary substances such as preservatives, antioxidants, pH buffering agents, surface active agents, and the like. Actual methods of preparing such dosage forms are known, or will be apparent, to those skilled in this art; for example, see *Remington's Pharmaceutical Sciences*, Mack Publishing Company, Easton, Pennsylvania, 15th Edition, 1975.

The formulation will preferably contain from about 0.01 to about 10% (w/w) active component. Application will preferably be from 1 to 4 times daily for periods up to about 6 months. Dosage and frequency will of course depend on the severity of the patient's acne and the judgment of the patients physician; however, a preferable regimen would be twice daily application of a formulation containing 2.5% active component.

When the compound is desired to diminish the conditions of cataracts, it may be administered topically directly to the eye in the form of drops of sterile, buffered ophthalmic solutions of pH 7.2–7.8. The administration can be conducted in single unit dosage form with continuous therapy or in single unit dosage therapy ad libitum. The formulation will preferably contain about 0.01% to about 10% (w/w) of a compound of Formula (I) with the remainder being suitable pharmaceutical excipients.

METHODS OF PREPARATION

The compounds of formula (I) are prepared by performing a sequence of reactions shown in Reaction Schemes I, II and III. Reaction Scheme I is preferred when a mixture of isomers is desired. Otherwise, Reaction Scheme II or III is used. The compounds of this invention are made by performing a (2+3) cycloaddition reaction between a preformed alkene substrate, such as 4 in Reaction Scheme I or 6 in Reaction Scheme II, and a halo-nitrile oxide (Step C in Reaction Scheme I and Step E in Reaction Scheme II) which is prepared in situ from the corresponding dibromoformaldoxime according to the general methods of P. A. Wade, M. K. Pillay, and S. M. Singh, Tetrahedron Lett., 1982, 4563; R. V. Stevens and R. P. Polniaszek, Tetrahedron Lett., 1983, 743; D. M. Vyas, Y. Chiang, and T. W. Doyle, Tetrahedron Lett., 1984, 487; and A. A. Hagedorn, B. J. Miller, and J. O. Nagy, Tetrahedron Lett., 1980, 229. The reagent dichloroformaldoxime is made according to the method of E. G. Trochimowski, K. Dymowski, and E. Schmidt, Bull. Soc. Chim. Fra. 1948, 597. Further derivatives such as esters, amides, peptides, etc., of the resulting 3-halo-4,5-dihydroisoxazole products 7, and 8, are made by standard peptide methodologies as found in "The Peptides: Analysis, Synthesis, and Biology", Vol. 1, 1979, Gross and Meienhofer, Ed., and "Chemistry of the Amino Acids", Vol. 2, 1961, Greenstein and Winitz, Ed., John Wiley and Sons.

An N-protected peptide or N-protected alpha-amino acid olefinic amide is made by coupling an olefinic amine and the N-protected peptide or N-protected alpha-amino acid with isobutyl chloroformate/N-methyl piperidine (see "The Peptides . . . ", above) or with EDCI/DMAP (see M. K. Dhaon, R. K. Olsen, and K. Ramasamy, J. Org. Chem., 1982, 47, 1962). The resulting unsaturated amide is then taken up in ethyl acetate containing a minimum amount of water and an excess of $NaHCO_3$ and treated with portions of dibromoformaldoxime as described by Vyas, et al. Work-up and purification on silica gel gives the desired 3-bromo-4,5-dihydroisoxazoles. For the chloro analogs, the general procedure involves the addition of small portions of $AgNO_3$ to a tetrahydrofuran (THF) solution at a temperature between about 60° C. and about 65° C. containing dichloroformaldoxime and the alkene. Standard work-up as described by Wade, et al. gives the desired 3-chloro-4,5-dihydroisoxazoles. The chloro analogs can also be prepared by performing an halogen exchange reaction with the 3-bromo-4,5-dihydroisoxazoles and a saturated HCl ether solution (see also K. C. Kelly, I. Schletter, S. J. Stein, W. Wierenga, J. Am. Chem. Soc., 1979, 101, 1054).

Isolation and purification of the compounds and intermediates described herein can be effected, if desired, by any suitable separation or purification procedure such as, for example, filtration, extraction, crystallization, column chromatography, thin-layer chromatography or thick-layer chromatography, or a combination of these procedures. Specific illustrations of suitable separation and isolation procedures can be had by reference to the Examples. However, other equivalent separation or isolation procedures could, of course, also be used.

The salt products are also isolated by conventional means. For example, the reaction mixtures may be evaporated to a dryness, and the salts can be further purified by conventional methods.

The compounds of Formula I in free base form may be converted to the acid addition salts by treating with a stoichiometric excess of the appropriate organic or inorganic acid, such as, for example, phosphoric, pyruvic, hydrochloric or sulfuric acid and the like. Typically, the free base is dissolved in a polar organic solvent such as ethanol or methanol, and the acid added thereto. The temperature is maintained between about 0° C. and 100° C. The resulting acid addition salt precipitates spontaneously or may be brought out of solution with a less polar solvent.

The acid addition salts of the compounds of Formula I may be decomposed to the corresponding free base by treating with a stoichiometric excess of a suitable base, such as potassium carbonate or sodium hydroxide, typically in the presence of aqueous solvent, and at a temperature of between about 0° C. and 100° C. The free base form is isolated by conventional means, such as extraction with an organic solvent.

Salts of the compounds of Formula I may be interchanged by taking advantage of differential solubilities of the salts, volatilities or acidities of the acids, or by treating with the appropriately loaded ion exchange resin. For example, the interchange is effected by the reaction of a salt of the compounds of Formula I with a slight stoichiometric excess of an acid of a lower pKa than the acid component of the starting salt. This conversion is carried out at a temperature between about 0° C. and the boiling point of the solvent being used as the medium for the procedure.

The salt derivatives of the compounds of Formula I are prepared by treating the corresponding free acids of the compounds of Formula I with at least one molar equivalent of a pharmaceutically acceptable base. Representative pharmaceutically acceptable bases are sodium hydroxide, potassium hydroxide, ammonium hydroxide, calcium hydroxide, trimethylamine, lysine, caffeine, and the like. The reaction is conducted in water, alone or in combination with an inert, water-miscible organic solvent, at a temperature of from about 0° C. to about 100° C., preferably at room temperature. Typical inert, water-miscible organic solvents include methanol, ethanol, or dioxane. The molar ratio of compounds of Formula I to base used are chosen to provide the ratio desired for any particular salt.

The compounds of the present invention may be prepared in either optically active form or as racemates or mixtures of diastereomers. Unless otherwise specified, the compounds described herein are all in the racemic form, or as a mixture of two diastereomers. The exception is the m-tyrosine analog since this amino acid is readily available commercially in D,L-form in which case a mixture of four isomers is obtained. However, the scope of the subject invention herein is not to be considered limited to mixtures of isomers, but to encompass the individual optical isomers of the compounds.

In most cases, individual isomers of Formula I are separated by semi-preparative HPLC on silica gel, eluting with ethyl acetate/hexane or other suitable solvents, or by performing fractional crystallizations. Alternatively, chiral resolutions of intermediates 7 or 8 with the aid of chiral resolving agents such as mandelic acid give pure isomers.

REACTION SCHEME I

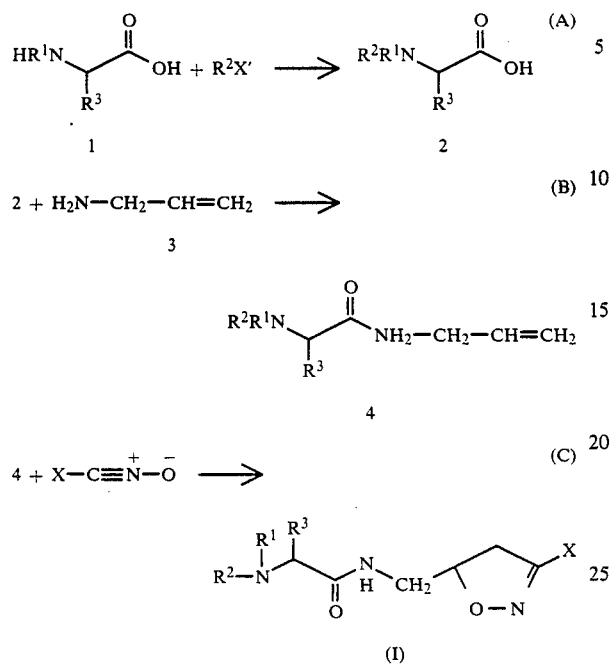

For each of the Reaction Schemes, $R^1$, $R^2$ and $R^3$ are commensurate in scope with the claims. $R^2X'$ is a reagent used to introduce an amino protecting group, corresponding to $R^2$, onto the amine functionality. $X'$ is a leaving group such as halogen. Suitable such reagents and protecting groups are well known to those skilled in the art.

Turning now to Reaction Scheme I, the starting material 2, is an N-protected alpha-amino acid, available commercially from Sigma Chemical Co., or other commercial houses, or can be synthesized from the unprotected amino acid 1 by derivatization of the amino group as shown in step A of Scheme I. N-alkyl amino acids may be obtained from commercial houses in some cases or made according to known methods (K. Barlos, D. Papaioannou, and D. Theodoropoulos, J. Org. Chem., 1982, 47, 1324; D. W. Hansen, Jr. and D. Pilipanskas, ibid, 1985, 50, 945; Y. Ohfune, N. Kurokawa, N. Higuchi, M. Saito, M. Hashimoto and T. Tanaka, Chem. Lett. 1984, 441; and F. M. F. Chen. and N. L. Benoiton, Can. J. Chem. 1977, 55, 1433).

Step A in Scheme I is directed to the substitution of the alpha-amino group. This step is a widely recognized standard operation in amino acid chemistry. For example, condensation of the alpha-amino acid 1 with BOC-ON, with benzyl chloroformate (both available from Aldrich Chemical Co.), with mesyl chloride or tosyl chloride, provides 2, with $R^2$ being the tert-butoxycarbonyl, benzyloxycarbonyl, mesyl or tosyl groups, respectively. Allyl amine 3 is available commercially.

Formation of the olefinic amide 4, step (B), involves the reaction of an activated version of compound 2. This step is a widely recognized standard operation in amino acid or peptide chemistry (see "The Peptides".. ., above). Hence the carboxyl group of compound 2 is activated by reacting with DCC, EDCI, N,N'-carbonyldiimidazole, isobutyl chloroformate/N-methyl piperidine or N-methyl morpholine, etc. The preferred method is the mixed anhydride coupling procedure utilizing isobutyl chloroformate/N-methyl piperidine. The resulting derivative treated with olefinic amine 3 yields the compound 4.

Step C involves the (2+3) cycloaddition reaction between a nitrile oxide reagent and the substrate olefin 4. For example, bromo nitrile oxide is generated in situ from dibromoformaldoxime and $NaHCO_3$. Dibromoformaldoxime is generated from glyoxic acid, hydroxyamine, and bromine in a one pot process according to the method of Vyas et al. The cycloaddition is carried out in an organic solvent, preferably EtOAc, at about 10° C. to about 30° C., but preferably at about 23° C., with 5 to 10 equivalents of $NaHCO_3$, preferably 6 equivalents, and containing about 2% to about 5% water. The dibromoformaldoxime is added in small portions over a 10 to 60 minute interval, preferably about 30 minutes. About 2 to about 4 equivalents are usually required to convert all of the starting material to products (I).

Isolation and purification of (I) are then accomplished by processing the reaction product. Thus, the organic phase is washed with water, 5% $NaHCO_3$, brine, and dried with $MgSO_4$. Filtration, concentration, and crystallization from ethyl acetate/hexane or chloroform/hexane provides crystalline product. Alternatively, purification by chromatography on $SiO_2$ may be required prior to the crystallization step.

The bromine atom in the 3-bromo-4,5-dihydroisoxazoles can be replaced by other groups such as alkoxy, alkylthio, alkylamino, or dialkylamino for instance, by reaction with sodium or lithium alkoxide, phenoxide, alkyl thiolate, phenyl thiolate, alkyl amides, or phenyl amides in an organic solvent such as tetrahydrofuran (THF) or methanol at about 20° C. to about 50° C. (see P. A. Wade J. Org. Chem., 1978, 43, 2020; J. E. Rowe and A. F. Hegarty, ibid, 1984, 49, 3083). Other nitrile oxide reagents may be employed in the (2+3) cycloaddition reaction. For example, 3-phenylsulfonyl-4,5-dihydroisoxazoles are made by reacting benzenesulfonylcarbonitrile oxide with olefinic substrates (see P. A. Wade, H. K. Yeu, S. A. Hardinger, M. K. Pillay, N. V. Amin, P. D. Vail, and S. D. Morrow, J. Org. Chem., 1983, 48, 1976, and P. A. Wade, and H. R. Hinney, J. Amer. Chem. Soc., 1979, 101, 1320). The —S(O)R and —S(O)$_2$R moieties can also be made by oxidizing 3-alkylthio- or 3-arylthio-4,5-dihydroisoxazoles with meta-chloroperbenzoic acid or with $KMnO_4$. The sulfonamide moiety (—S(O)$_2$NH$_2$, —S(O)$_2$NHR) is made by chloroamine treatment of 3-thio-4,5-dihydroisoxazoles followed by oxidation.

In the case where X is chlorine, the cycloaddition is preferably carried out in THF at about 50° C. to about 70° C., preferably about 60° C., by adding about 4 to about 6 equivalents of $AgNO_3$, preferably in small portions to the alkene substrate and the dichloroformaldoxime reagent according to the method of Wade, et al. After total conversion of starting alkene, $CH_2Cl_2$ is added, and the reaction mixture is filtered through celite and concentrated. Isolation and purification of product proceeds as above.

REACTION SCHEME II

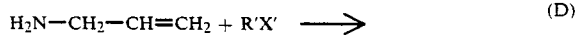

(D)

3

-continued
REACTION SCHEME II

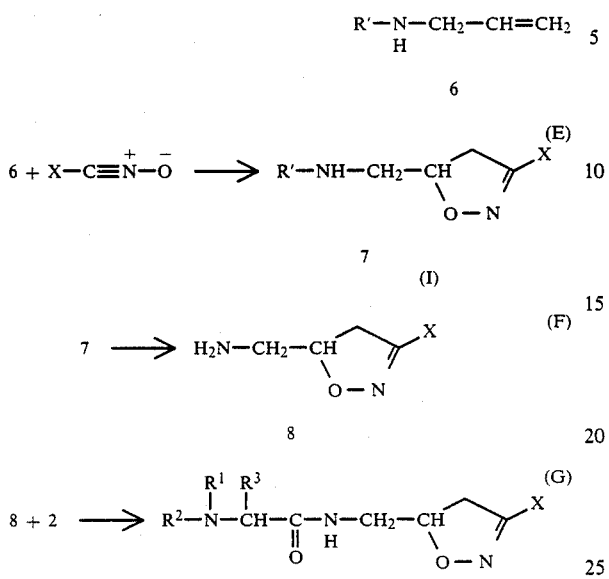

Reaction Scheme II illustrates an alternative sequence to generate products of Formula I. Hence, an olefinic amine is treated in step D with R'X', wherein R' is commensurate in scope with $R^2$ and X' is a leaving group such as halogen, to protect/derivatize the amino group. This is accomplished in the same manner as step A in Scheme I. In this case di-tert-butyldicarbonate is preferred. Hence, addition of one equivalent of the latter reagent to the amine 3 in an organic solvent, preferably ether or $CH_2Cl_2$, at room temperature gives 6 after concentration of the reaction mixture.

Step E involves the (2+3) cycloaddition reaction exactly in the same manner as described above. The substituent X is preferably replaced at this stage with other groups such as methoxy, ethylthio, etc. (when X=Br in 7), by treating 7 with the corresponding lithium or sodium methoxide, ethylthiolate, etc., preferably in THF or methanol at about 20° to about 50° C.; most preferably at about 25° C.

Step F involves removing the amino protecting group, i.e., R' in 7. In the case where $R^2$ is Boc, this step can be accomplished in any of several ways, for example, with: 20% $CF_3CO_2H$ in $CH_2Cl_2$; formic acid (neat); toluene sulfonic acid in ether or ethyl acetate; or HCl in ether, THF, or ethyl acetate. In the case where $R^2$ is Cbz, this step is preferably accomplished with $CF_3CO_2H$ in anisole (see R. B. Silverman, M. W. Holladay, J. Am. Chem. Soc., 1981, 103, 7357). Other methods known in the art for the removal of R' can be used, such as hydrogenation, hydrofluoric acid, and the like. The amine 8 can be resolved at this stage as the mandelic acid salt.

If desired, the intermediates 7 and 8 herein may be separated into pure stereoisomers by conventional resolution means; for example by separation (e.g. fractional crystallization) of the diastereomeric salts formed by the reaction of these compounds with optically active acids. Exemplary of such optically active acids are the optically active forms of camphor-10-sulfonic acid, 2-bromo-camphor-π-sulfonic acid, camphoric acid, menthoxyacetic acid, tartaric acid, malic acid, mandelic acid, diacetyltartaric acid, pyrrolidine-5-carboxylic acid and the like.

Step G involves the condensation of the amine 8 with an N-protected alpha-amino acid or peptide to give the compounds of Formula I, preferably via the mixed anhydride method as described above. The reaction can be carried out in an appropriate polar organic solvent at a temperature of about 0° C. to −20° C. For example, N-benzyloxycarbonyl L-phenylalanine in $CH_2Cl_2$ at −20° C. is treated with N-methyl piperidine or N-methyl morpholine and then isobutyl chloroformate. Amine 8 in $CH_2Cl_2$ is then added and the reaction mixture brought to room temperature. Work-up by washing with water, 5% HCl, 5% $NaHCO_3$, and drying of the organic phase gives the desired coupled product.

REACTION SCHEME III

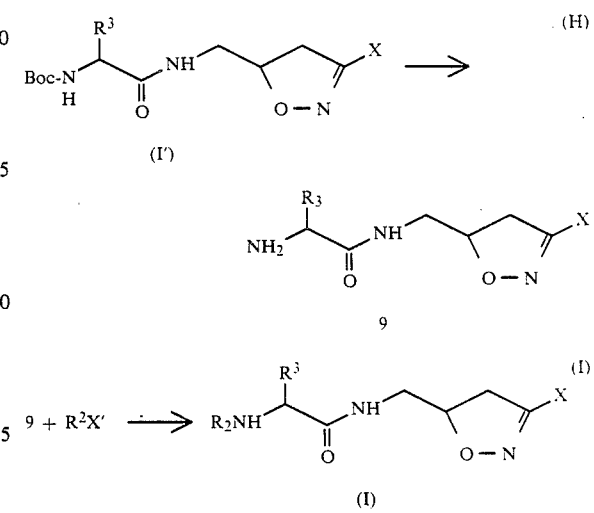

Compounds of Formula (I) can also be made by utilizing Reaction Scheme III. In this scheme, a compound of Formula (I') is treated with a deblocking reagent such as 20% trifluoroacetic acid in an organic solvent such as $CH_2Cl_2$ at a temperature of between 0° C. to 20° C. to generate the trifluoroacetic acid salt of amine 9. It can also be treated with tosic acid in an organic solvent at a temperature of between 30° C. to 60° C. (such as refluxing ethyl acetate) to generate the tosic acid salt of amine 9. The methodology is the same as in step (F) (scheme II). Step (I) involves taking amine 9 in an organic solvent such as $CH_2Cl_2$ at a temperature of between 0° C. to 20° C. and then treating with $R^1X'$ or $R^2X'$ as in step (A) (scheme I) or step (D) (scheme II) to generate target compounds (I) having $R_2$ other than Boc. These compounds can also be obtained via scheme I or scheme II.

In the following preparations, N-protected alpha-amino acids were supplied from commercial houses such as Sigma Chemical Co., Chemical Dynamics Corp., Bachem Inc., etc., or were prepared by known procedures. For example, Cbz (M. Bergman, L. Zervas, Ber. Dtsch. Chem. Ges., 1932, 65, 1192; see also Greenstein and Winitz); Boc (M. Itoh, D. Hagiwara, T. Kamiya Tetrahedron Lett., 1975, 4393); Fmoc (L. Lapatsanis, G. Milias, K. Froussios, M. Kolovos, Synthesis 1983, 671). The following experimental details are illustrative and should not be understood as limiting the scope of the invention.

PREPARATION 1 (Step A - Scheme I)

N-benzyloxycarbonyl-meta-tyrosine

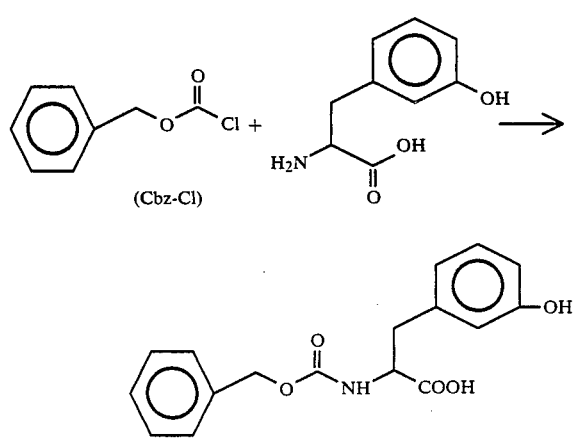

To an ice cold aqueous solution of D,L-meta-tyrosine, 3.0 gm, was added portion-wise carbobenzoxy chloride, 2.6 ml, and NaOH, 4.2 ml, maintaining the pH around 9.0. Upon completion of the reaction, the reaction mixture was extracted once with ether, 25 ml. The aqueous portion was then acidified to Congo Red with 5M HCl in a two phase system containing $CH_2Cl_2$. Further extraction of the aqueous portion thrice with $CH_2Cl_2$ (25 ml), followed by washing of the combined organic extracts with water (20 ml), brine (20 ml), drying over anhydrous $MgSO_4$, and concentration, gave 1.8 gm of product. IR (neat): 3500–2400 (broad, OH, COOH, NH), 1740–1680 (CO). 1H NMR (80 MHz, $CDCl_3$): delta 3.05 (AB, 2H, $CH_2$), 4.6 (m, 1H, CH), 5.1 (s, 2H, $PhCH_2O$), 5.3 (broad d, 1H, NH), 6.25 (broad s, 2H, OH, COOH), 6.6–7.3 ppm (m, 4H, Ph).

By substituting other amino acids for D,L-meta-tyrosine, other intermediates can be formed having the N-benzyloxycarbonyl protecting group. For example, any naturally occurring amino acid can be used, such as glycine, alanine, valine, leucine, isoleucine, serine, threonine, phenylalanine, para- and ortho-tyrosines, tryptophan, cysteine, aspartic acid, asparagine, glutamic acid, glutamine, histidine, arginine, homoarginine, lysine, hydroxysine, ornithine, homoserine, dihydroxyphenylalanine (DOPA), and the like. For those amino acids bearing a secondary functionality in the side chain, such as amino, carboxyl, hydroxyl, thiol, imidazole or indole, an additional protecting and deprotecting step is required, as is known in the art. Further, synthetic amino acids can be used, such as the substituted homoarginines disclosed in U.S. Pat. No. 4,481,190, to Nestor, et al., hereby incorporated fully into this specification by reference; or the meta-and para- cyanophenylalanine derivatives described by Wagner et al. in Pharmazie 29, 12 (1974) and 36, 597 (1981), and which serve as precursors to amidine, COOH, $CONH_2$, etc. analogs.

Additionally, any of a variety of protecting groups can be used in conjuction with the above-named (or other) amino acids, including Boc, Cbz, benzoyl, toluenesulfonyl, biphenylisopropyloxycarbonyl, o-nitrophenylsulfenyl, 2-cyano-t-butyloxycarbonyl, Fmoc, and the like.

Moreover, $R^2$ can be varied by varying the starting material. For example, a dipeptide rather than a single amino acid residue can be used in place of the meta-tyrosine used in this preparation, to yield a protected dipeptide of the formula:

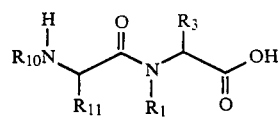

where the substituents are as defined in the summary. Further, reductive alkylation of an O-protected amino acid with a carbonyl reagent such as acetophenone, butanal, pentanal, and the like, using sodium cyanoborohydride, for example, will yield corresponding alkyl variations of $R^1$ and $R^2$.

By way of example, the following derivatized amino acids are prepared by this preparation method:
N-benzyloxycarbonyl-L-phenylalanine;
N-benzyloxycarbonyl-L-para-tyrosine;
N-benzyloxycarbonyl-L-ortho-tyrosine;
N-benzyloxycarbonyl-D-naphthylalanine;
N-benzyloxycarbonyl-D-para-chlorophenylalanine;
N-tert-butoxycarbonyl-L-phenylalanine;
N-benzyloxycarbonyl-L-aspartic acid;
N-benzyloxycarbonyl-N-ε-tert-butoxycarbonyl-L-lysine;
N-benzyloxycarbonyl-β-benzyl-L-aspartic acid;
N-acetyl-L-naphthylalanine;
N-benzyloxycarbonyl-glycine;
N-benzyloxycarbonyl-L-isoleucine;
N-[9-fluorenylmethyloxycarbonyl]-L-phenylalanine;
N-tert-butoxycarbonyl-O-benzyl-L-threonine;
N-benzyloxycarbonyl-L-threonine;
N-benzyloxycarbonyl-L-alanyl-L-phenylalanine;
N-benzoyl-L-phenylalanine;
N-benzyloxycarbonyl-D-phenylalanine;
N-benzyloxycarbonyl-L-naphthylmethylglycine;
N-benzyloxycarbonyl-L-γ-glutamine;
N-phthaloyl-L-phenylalanine;
N-benzyloxycarbonyl-D,L-meta-tyrosine;
N-benzyloxycarbonyl-L-meta-tyrosine;
N-benzyloxycarbonyl-L-2-methoxyphenylalanine;
N-benzyloxycarbonyl-L-3-methoxyphenylalanine;
N-benzyloxycarbonyl-L-3,4-dihydroxyphenylalanine;
N-benzyloxycarbonyl-L-3-methoxytyrosine;
N-benzyloxycarbonyl-L-4-methoxyphenylalanine;
N-benzyloxycarbonyl-L-tryptophan; and
N-benzyloxycarbonyl-L-5-hydroxytryptophan.

PREPARATION 2 (Step B - Scheme I)

N-benzyloxycarbonyl-L-phenylalanine allyl amide

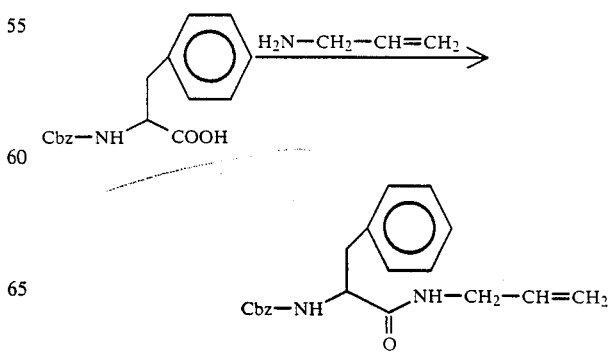

The following experimental details are exemplary of the olefinic amide preparations and derivations of the 3-halo-4,5-dihydroisoxazoles.

Allyl amine, 0.8 ml, was added to an ice cold solution of N-benzyloxycarbonyl-L-phenylalanine, 3.0 gm, 1-(3-dimethylaminopropyl)-3-ethylcarbodiimide hydrochloride (EDCI), 4.7 gm, and 4-dimethylaminopyridine (DMAP), 30 mg, in 50 ml of ethyl acetate with stirring. After 30 minutes, the reaction mixture was brought to room temperature and then left overnight. The reaction mixture was then further diluted with ethyl acetate and washed twice with 20 ml portions of 5% HCl, water, 5% NaHCO3, and brine. Drying of the organic portion with anh. MgSO4 and concentration gave a residue which crystallized on standing; $[\alpha]_D^{23} = +1.9°$ C. An alternative procedure also used in the synthesis of the title amide involves the mixed anhydride method (see N. L. Benoiton, et al., J. Org. Chem., 1985, 48. 2939, and Org. Reactions, Vol. 12, pp. 195, 1962).

The allyl amides corresponding to the derivatized amines set forth in Preparation 1 are prepared by this method:

N-benzyloxycarbonyl-L-phenylalanine allyl amide;
N-benzyloxycarbonyl-L-para-tyrosine allyl amide;
N-benzyloxycarbonyl-L-ortho-tyrosine allyl amide;
N-benzyloxycarbonyl-D-naphthylalanine allyl amide;
N-benzyloxycarbonyl-D-para-chlorophenylalanine allyl amide;
N-tert-butoxycarbonyl-L-phenylalanine allyl amide;
N-benzyloxycarbonyl-L-aspartic acid allyl amide;
N-benzyloxycarbonyl-N-ε-tert-butoxycarbonyl-L-lysine allyl amide;
N-benzyloxycarbonyl-β-benzyl-L-aspartic acid allyl amide;
N-acetyl-L-naphthylalanine allyl amide;
N-benzyloxycarbonyl-glycine allyl amide;
N-benzyloxycarbonyl-L-isoleucine allyl amide;
N-[9-fluorenylmethyloxycarbonyl]-L-phenylalanine allyl amide;
N-tert-butoxycarbonyl-O-benzyl-L-threonine allyl amide;
N-benzyloxycarbonyl-L-threonine allyl amide;
N-benzyloxycarbonyl-L-alanyl-L-phenylalanine allyl amide;
N-benzoyl-L-phenylalanine allyl amide;
N-benzyloxycarbonyl-D-phenylalanine allyl amide;
N-benzyloxycarbonyl-L-naphthylmethylglycine allyl amide;
N-benzyloxycarbonyl-L-γ-glutamine allyl amide;
N-phthaloyl-L-phenylalanine allyl amide;
N-benzyloxycarbonyl-D,L-meta-tyrosine allyl amide;
N-benzyloxycarbonyl-L-meta-tyrosine allyl amide;
N-benzyloxycarbonyl-L-2-methoxyphenylalanine allyl amide;
N-benzyloxycarbonyl-L-3-methoxyphenylalanine allyl amide;
N-benzyloxycarbonyl-L-4-methoxyphenylalanine allyl amide;
N-benzyloxycarbonyl-L-3,4-dihydroxyphenylalanine allyl amide;
N-benzyloxycarbonyl-L-tryptophan allyl amide;
N-benzyloxycarbonyl-L-3-methoxytyrosine allyl amide;
N-benzyloxycarbonyl-L-5-hydroxytryptophan allyl amide;
N-benzyloxycarbonyl-L-phenylalanyl-L-alanine allyl amide; and
N-benzyloxycarbonyl-L-alanyl-L-phenylalanine allyl amide.

PREPARATION 3 (Step D - Scheme II)

N-tertbutoxycarbonyl allyl amine

Di-tert-butyldicarbonate, 64 gm, was added portionwise at room temperature to allyl amine, 22 ml, in 400 ml of CH2Cl2 with stirring. The reaction mixture was left overnight and then concentrated to give an oil which solidified on standing. IR(KBr): 3340, 2962, 1690, 1509 cm$^{-1}$. $^1$H NMR (80 MHz, CDCl3): delta 1.45 (s, 9H, t-butyl), 3.6–3.9 (m, 2H, CH2N), 4.34–4.8 (broad s, 1H, NH), 5.0–5.3 (m, 2H, CH2=C), 5.6–6.1 (m, 1H, —CH=C).

N-benzyloxycarbonyl allyl amine was made in the same manner by utilizing benzyl chloroformate and triethylamine at 0° C. Cbz chloride, tosyl chloride, phthaloyl chloride and benzoyl chloride can similarly be used to obtain the corresponding allyl amine.

PREPARATION 4 (Step E - Scheme II)

5-(N-tert-butoxycarbonyl-aminomethyl)-3-bromo-4,5-dihydroisoxazole $$(CH_3)_3C-O-\overset{O}{\underset{\|}{C}}-NH-CH_2-CH=CH_2 \xrightarrow{Br-C\equiv N-O}$$

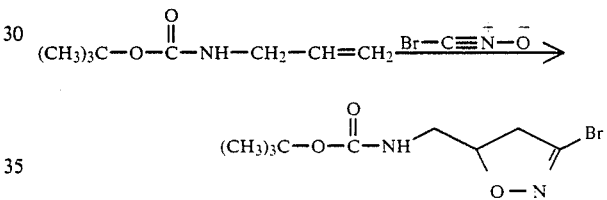

To a solution of N-tert-butoxycarbonyl allyl amine, 20 gm, in 700 ml of ethyl acetate and containing 65 gm of NaHCO3 and 50 ml of water, was added portion-wise 80 gm of dibromoformaldoxime at room temperature with vigorous stirring. After completion of the reaction, the organic portion was washed with water (2×100 ml), 100 ml each of 5% NaHCO3, brine and dried over anh. MgSO4 and concentrated to give an oil. Purification by chromatography on silica gel gave the desired product as an oil which solidified on standing. IR(KBr): 3322, 2988, 1680, 1529 cm$^{-1}$. $^1$H NMR (80 MHz, CDCl3): delta 1.45 (s, 9H, t-butyl), 2.8–3.5 (m, 4H, CH2CHO, CH2N), 4.6–5.1 (broad s, superimposed on a multiplet, 2H, NH, CHO).

By substituting N-benzyloxycarbonylallyl amine for N-tert-butoxycarbonyl allyl amine, the following compounds are made:

5-(N-benzyloxycarbonylaminomethyl)3-chloro-4,5-dihydroisoxazole; and
5-(N-benzyloxycarbonylaminomethyl)3-bromo-4,5-dihydroisoxazole.

These intermediates are active as transglutaminase inhibitors.

Similarly, N-phthaloyl allyl amine, N-benzoyl allyl amine, N-tosyl allyl amine or N-mesyl allyl amine can be used to yield the corresponding substituted dihydroisoxazoles.

PREPARATION 5 (Step F - Scheme II)

5-Aminomethyl-3-bromo-4,5-dihydroisoxazole

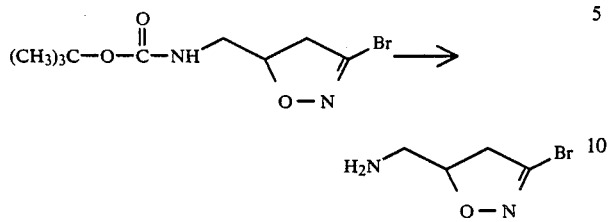

N-tert-butoxycarbonyl-5-aminomethyl-3-bromo-4,5-dihydroisoxazole, 20 gm, was taken up in 400 ml of 20% $CF_3CO_2H/CH_2Cl_2$ at 0°. After 14 hrs, the reaction mixture was evacuated to an oil. The oil was taken up in 5% $Na_2CO_3$ and the resulting basic solution was extracted repeatedly (5×40 ml) with $CH_2Cl_2$. The organic portions were combined, washed once with 30 ml of water, brine, dried over anh. $MgSO_4$ and concentrated to give a light yellow oil. $^1$H NMR (80 MHz, $CDCl_3$): delta 1.2–1.4 (broad s, 2H, $NH_2$), 2.7–3.5 (m, 2H, $CH_2CHO$), 3.1 (dd, 2H, J=8 Hz, $CH_2N$), 4.65–4.9 (m, 1H, CHO). The tartaric acid salt had: $^1$H NMR (80 MHz, $D_2O$): delta 3.0–3.8 (ABX, 2H, $CH_2CHO$), 3.25 (broad d, 2H, J=6.5 Hz, $CH_2N$), 4.5 (s, 2H, CH of tartaric acid), 4.8–5.2 ppm (m, 1H, CHO). $^{13}$C NMR (20 MHz, $D_2O$): delta 179.1 (CO), 143.4 (BrC=N), 80.43 (CHO), 75.6 (CHO of tartaric acid), 47.2 ($CH_2$), 44.6 ppm ($CH_2$).

In the same manner the following amines were made: 5-aminomethyl-3-methoxy-4,5-dihydroisoxazole; and 5-aminomethyl-3-ethylthiyl-4,5-dihydroisoxazole. 5-aminomethyl-3-ethylsulfonyl-4,5-dihydroisoxazole.

In the case of S(O)R or $S(O)_2R$, the compounds can be made by oxidizing 3-alkylthio- or 3-arylthio-4,5-dihydroisoxazoles with MCPBA or with $KMnO_4$; the latter class can also be obtained by the cycloaddition reaction set forth in this preparation. The sulfonamide moiety can be made by chloroamine treatment of 3-thiyl-4,5-dihydroisoxazoles followed by oxidation.

PREPARATION 6

Resolution of 5-aminomethyl-3-bromo-4,5-dihydroisoxazole

The title compound was resolved as the mandelic acid salt. Hence 5-aminomethyl-3-bromo-4,5-dihydroisoxazole was taken up in ethanol and the solution was added to 1.0 equivalent of d-mandelic acid in methanol. Crystallization from ethanol-water gave as the first crop, only one isomer of the mandelic acid salt of 5-aminomethyl-3-bromo-4,5-dihydroisoxazole.
$[\alpha]_D^{23} = +120.6$ ($H_2O$). Basification of the salt with 5% $Na_2CO_3$, extraction with $CH_2Cl_2$ as above gave the free amine optically pure $[\alpha]_D^{23} = +208.6$ ($CH_2Cl_2$).

PREPARATION 7 (Step F - Scheme II)

5-Aminomethyl-3-chloro-4,5-dihydroisoxazole hydrochloride

A solution of N-t-butoxycarbonyl-5-aminomethyl-3-bromo-4,5-dihydroisoxazole 2, 12 gm in 300 mL of anhydrous THF was cooled to 0° (ice bath). Anhydrous HCl 5 to 6 gm (large excess) was bubbled in over a period of about 1 hour. The cooling bath was then removed and the flask was left stoppered to stir for four days. The product was collected by filtration and the crystalline material washed well with an ether/hexane solution. Further product was obtained by condensing the filtrate and collecting the solid precipitate by filtration. The solid material was combined to afford 5.9 gm of 3-chloro-dihydroisoxazole hydrochloride salt. Note: The progress of the reaction can be monitored by observing the appearance of the 3-chlorine signal (approximately 154.9 ppm) concomitant with the disappearance of the 3-bromine signal in the $^{13}$C NMR spectra.

PREPARATION 8

N-tert-butoxycarbonyl-5-aminomethyl-3-methoxy-4,5-dihydroisoxazole

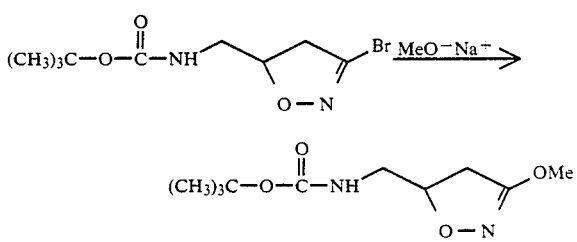

To a solution of N-tert-butoxycarbonyl-5-aminomethyl-3-bromo-4,5-dihydroisoxazole, 317 mg, in 30 ml of anhydrous methanol, stirring under nitrogen, was added sodium methoxide, 184 mg, at room temperature. The course of the reaction was followed by tlc. After 48 hrs, a further 61 mg of sodium methoxide were added and after 50 hrs, the reaction was quenched with 20 ml of a saturated solution of ammonium chloride. The methanol was removed in the rotary evaporator and the resulting residue was taken up in 30 ml of $CH_2Cl_2$, and washed with water and brine. Drying over anh. $MgSO_4$ and concentration gave product as a clear colorless oil. IR(neat): 3350, 2980, 1710, 1631, 1520 cm$^{-1}$. $^1$H NMR (80 MHz, $CDCl_3$): delta 4.92 (broad s, 1H, NH), 4.48–4.81 (m, 1H, CHO), 3.78 (s, 3H, OMe), 3.21–3.39 (m, 2H, $CH_2N$), 2.69–2.81 (m, 2H, $CH_2CHO$), 1.37 (s, 9H, t-butyl).

In the same manner, N-tert-butoxycarbonyl-5-aminomethyl-3-ethylthiyl-4,5-dihydroisoxazole was made by using sodium ethyl thiolate in dry DMF instead of sodium methoxide in methanol.

EXAMPLE 1 (Step C - Scheme I)

5-(N-benzyloxycarbonyl-L-phenylalaninamidomethyl)-3-bromo-4,5-dihydroisoxazole

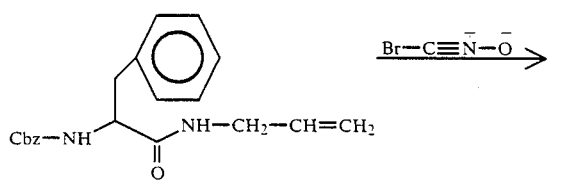

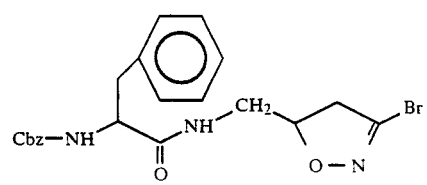

To a solution of N-benzyloxycarbonyl-L-phenylalanine allyl amide, 700 mg, in 40 ml of EtOAc and 0.75 ml of water, was added 870 mg of NaHCO$_3$ and in small portions, dibromoformaldoxime, 631 mg. The progress of the reaction was monitored by tlc (40% EtOAc/hexane). After completion of the reaction (2-4 hrs), the reaction mixture was transferred to a separatory funnel and washed repeatedly with 5% NaHCO$_3$, brine, and dried over anh. MgSO$_4$. Filtration and concentration gave a light yellow viscous oil. Purification by chromatography on silica gel (15% EtOAc/hexane) gave product as a 1:1 mixture of stereoisomers. Crystallization from CHCl$_3$/hexane gave crystalline product, m.p. 122°–125° C. Anal. Calcd for C$_{21}$H$_{22}$BrN$_3$O$_4$: C, 54.79; H, 4.82; N, 9.13. Found: C, 54.82; H, 4.70; N, 8.94. $^{13}$C NMR (20 MHz, CDCl$_3$): delta 172.0, 171.9 (CON), 155.82 (OCONH), 137.7, 137.6 (BrC=N), 136.2, 135.9 (Ph), 126.9–129.2 (Ph), 80.2 (CHO), 66.9 (PhCH$_2$O), 56.3 (CHN), 43.8, 43.6 (CH$_2$CHO), 41.4, 41.6 (CH$_2$N), 38.4, 38.5 (PhCH$_2$). The individual isomers were separated by HPLC on silica gel. More polar isomer: m.p., 151°–153° C. IR (KBr): 3320, 1690, 1650, 1522 cm$^{-1}$. $^1$H NMR (80 MHz, CDCl$_3$): delta 7.12–7.41 (m, 10H, Ph), 6.18–6.41 (m, 1H, NH), 5.27 (d, 1H, NH), 5.07 (s, 2H, PhCH$_2$O), 4.55–4.92 (:m, 1H, CHO), 4.28–4.56 (m, 1H, CHN), 3.4–3.57 (m, 2H:, CH$_2$NH), 3.08 (d, 2H, PhCH$_2$), 2.62–3.21 (m, 2H, CH$_2$CHO). $[\alpha]_D^{23}$ = +49.6 (c 0.03, CHCl$_3$). Less polar isomer: m.p. 155°–157° C. IR (KBr): 3320, 1688, 1650, 1528 cm$^{-1}$. $^1$H NMR (300 MHz, CDCl$_3$): delta 7.13–7.39 (m, 10H, Ph), 6.21–6.28 (broad, 1H, NH), 5.23 (d, 1H, NH), 5.1 (s, 2H, PhCH$_2$O), 4.66–4.78 (m, 1H, CHO), 4.37–4.46 (m, 1H, CHN), 3.46–3.53 (m, 2H, CH$_2$N), 3.17 (dd, 1H, CHCHO), 3.08 (d, 2H, PhCH$_2$), 2.84 (dd, 1H, CHCHO). $[\alpha]_D^{23}$ = −58.7° C. (c 0.03, CHCl$_3$).

In a similar manner, using the precursors listed in Preparation 2, the corresponding 3-bromo-4,5-dihydroisoxazoles are prepared:

5-(N-benzyloxycarbonyl-L-phenylalaninamidomethyl)-3-bromo-4,5-dihydroisoxazole;
5-(N-benxyloxycarbonyl-L-para-tyrosinamidomethyl)-3-bromo-4,5-dihydroisoxazole;
5-(N-benzyloxycarbonyl-L-ortho-tyrosinamidomethyl)-3-bromo-4,5-dihydroisoxazole;
5-(N-benzyloxycarbonyl-D-naphthylalaninamidomethyl)-3-bromo-4,5-dihydroisoxazole;
5-(N-benzyloxycarbonyl-D-para-chlorophenylalaninamidomethyl)3-bromo-4,5-dihydroisoxazole;
5-(N-tert-butoxycarbonyl-L-phenylalaninamidomethyl)-3-bromo-4,5-dihydroisoxazole;
5-(N-benzyloxycarbonyl-L-aspartic acid-α-amidomethyl)-3-bromo-4,5-dihydroisoxazole;
5-(N-benzyloxycarbonyl-L-glutamic acid-α-amidomethyl)-3-bromo-4,5-dihydroisoxazole;
5-(N-benzyloxycarbonyl-5-(N-ϵ-tert-butoxycarbonyl-L-lysinamidomethyl)3-bromo-4,5-dihydroisoxazole;
5-(N-benzyloxycarbonyl-β-benzyl-L-aspartic acid-amidomethyl)-3-bromo-4,5-dihydroisoxazole;
5-(N-acetyl-L-naphthylalaninamidomethyl)-3-bromo-4,5-dihydroisoxazole;
5-(N-benzyloxycarbonyl-glycinamidomethyl)-3-bromo-4,5-dihydroisoxazole;
5-(N-benzyloxycarbonyl-L-isoleucinamidomethyl)-3-bromo-4,5-dihydroisoxazole;
5-(N-[9-fluorenylmethyloxycarbonyl]-L-phenylalaninamidomethyl)3-bromo-4,5-dihydroisoxazole;
5-(N-tert-butoxycarbonyl-O-benzyl-L-threoninamidomethyl)3-bromo-4,5-dihydroisoxazole;
5-(N-benzyloxycarbonyl-L-threoninamidomethyl)-3-bromo-4,5-dihydroisoxazole;
5-(N-benzyloxycarbonyl-L-alanyl-L-phenylalaninamidomethyl)3-bromo-4,5-dihydroisoxazole;
5-(N-benzoyl-L-phenylalaninamidomethyl)-3-bromo-4,5-dihydroisoxazole;
5-(N-benzyloxycarbonyl-D-phenylalaninamidomethyl)-3-bromo-4,5-dihydroisoxazole;
5-(N-benzyloxycarbonyl-L-naphthylmethyl-glycinamidomethyl)3-bromo-4,5-dihydroisoxazole;
5-(N-benzyloxycarbonyl-L-γ-glutaminamidomethyl)-3-bromo-4,5-dihydroisoxazole;
5-(N-phthaloyl-L-phenylalaninamidomethyl)-3-bromo-4,5-dihydroisoxazole;
5-(N-benzyloxycarbonyl-D,L-meta-tyrosinamidomethyl)-3-bromo-4,5-dihydroisoxazole;
5-(N-benzyloxycarbonyl-L-meta-tyrosinamidomethyl)-3-bromo-4,5-dihydroisoxazole;
5-(N-benzyloxycarbonyl-L-2-methoxyphenylalaninamidomethyl)-3-bromo-4,5-dihydroisoxazole;
5-(N-benzyloxycarbonyl-L-3-methoxyphenylalaninamidomethyl)-3-bromo-4,5-dihydroisoxazole;
5-(N-benzyloxycarbonyl-L-4-methoxyphenylalaninamidomethyl)-3-bromo-4,5-dihydroisoxazole;
5-(N-benzyloxycarbonyl-L-3,4-dihydroxyphenylalaninamidomethyl)-3-bromo-4,5-dihydroisoxazole;
5-(N-benzyloxycarbonyl-L-tyrptophanamidomethyl)-3-bromo-4,5-dihydroisoxazole;
5-(N-benzyloxycarbonyl-L-5-hydroxytryptophanamidomethyl)-3-bromo-4,5-dihydroisoxazole;
5-(N-benzyloxycarbonyl-L-3-methoxytyrosinamidomethyl)-3-bromo-4,5-dihydroisoxazole;
5-(N-benzyloxycarbonyl-L-3-methoxytyrosinamidomethyl)-3-bromo-4,5-dihydroisoxazole;
5-(N-benzyloxycarbonyl-L-phenylalanyl-L-alaninamidomethyl)-3-bromo-4,5-dihydroisoxazole; and
5-(N-benzyloxycarbonyl-L-alanyl-L-phenylalaninamidomethyl)-3-bromo-4,5-dihydroisoxazole.

EXAMPLE 2 (Step C - Scheme I)

5-(N-benzyloxycarbonyl-L-phenylalaninamidomethyl)-3-chloro-4,5-dihydroisoxazole

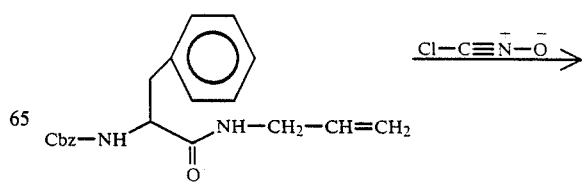

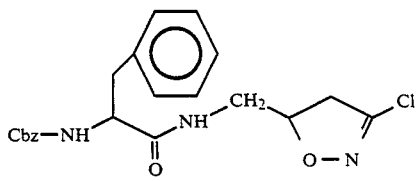

Silver nitrate, 2.0 gm, was added slowly to a mixture of N-benzyloxycarbonyl-L-phenylalanine allyl amide, 1 gm, and dichloroformaldoxime, 1.1 gm, in 120 ml of dry THF, with stirring. The reaction temperature was maintained at about 60°–65° C. for 1.5 hrs, CH$_2$Cl$_2$, 50 ml, was then added and the reaction mixture was filtered through celite. The solvent was removed and the residue taken up in CH$_2$Cl$_2$ and the organic phase washed with 5% NaHCO$_3$, brine, dried over anh. MgSO$_4$ and concentrated. Crystallization from CH$_2$Cl$_2$/hexane gave product as a mixture of two stereoisomers. The individual isomers were separated by HPLC on silica gel. More polar isomer: m.p. 141°–148° C. IR(KBr): 3319, 1690, 1654, 1540, 1522 cm$^{-1}$. $^1$H NMR (80 MHz, CDCl$_3$): delta 7.1–7.3 (m, 10H, Ph), 6.2–6.45 (t, 1H, NH), 5.2–5.38 (d, 1H, NH), 5.07 (s, 2H, PhCH$_2$O), 4.61–4.94 (m, 1H, CHO), 4.27–4.58 (m, 1H, CHN), 3.44–3.57 (dd, 2H, CH$_2$N), 3.08 (d, 2H, CH$_2$Ph), 2.56–3.08 ppm (m, 2H, CH$_2$CHO). $^{13}$C NMR (20 MHz, CDCl$_3$): delta 171.9 (CONH), 155.8 (OCONH), 149.4 ((BrC=N), 136.1, 127–129.2 (Ph), 80.8 (CHO), 67.0 (PhCH$_2$O), 56.3 (CHN), 41.4 (CH$_2$NH), 40.6 (CH$_2$CHO), 38.4 (PhCH$_2$). $[\alpha]_D^{23}$ = +46.7° C. (c 0.031, CHCl$_3$). Less polar isomer: m.p. 140°–141° C. IR(KBr): 3310, 1688, 1655, 1530, 1282 cm$^{-1}$. $^1$H NMR (80 MHz, CDCl$_3$): delta 7.1–7.3 (m, 10H, Ph), 6.18–6.5 (broad, 1H, NH), 5.2–5.4 (d, 1H, NH), 5.08 (s, 2H, PHCH$_2$O), 4.58–4.88 (m, 1H, CHO), 4.25–4.53 (m, 1H, CHN), 3.38–3.58 (dd, 2H, CH$_2$NH), 3.07 (d, 2H, PhCH$_2$), 2.66–3.05 (m, 2H, CH$_2$CHO). $^{13}$C NMR (20 MHz, CDCl$_3$): delta 171.9 (CONH), 155.8 (OCONH), 149.3 (BrC=N), 136.0, 136.1, 126.9–129.1 (Ph), 80.8 (CHO), 66.9 (PhCH$_2$O), 56.3 (CHN), 41.6 (CH$_2$N), 40.8 (CH$_2$CHO), 38.4 ppm (PhCH$_2$). $[\alpha]_D^{23}$ = −61.8 (0.03, CHCl$_3$).

In a similar manner, using the precursors listed in Preparation 2, the corresponding 3-chloro-4,5-dihydroisoxazoles are prepared:

5-(N-benzyloxycarbonyl-L-phenylalaninamidomethyl)-3-chloro-4,5-dihydroisoxazole;

5-(N-benzyloxycarbonyl-L-para-tyrosinamidomethyl)-3-chloro-4,5-dihydroisoxazole;

5-(N-benzyloxycarbonyl-L-ortho-tyrosinamidomethyl)-3-chloro-4,5-dihydroisoxazole;

5-(N-benzyloxycarbonyl-D-naphthylalaninamidomethyl)-3-chloro-4,5-dihydroisoxazole;

5-(N-benzyloxycarbonyl-D-para-chlorophenylalaninamidomethyl)3-chloro-4,5-dihydroisoxazole;

5-(N-tert-butoxycarbonyl-L-phenylalaninamidomethyl)-3-chloro-4,5-dihydroisoxazole;

5-(N-benzyloxycarbonyl-L-aspartic acid-amidomethyl)-3-chloro-4,5-dihydroisoxazole;

5-(N-benzyloxycarbonyl-5-(N-ε-tert-butoxycarbonyl-L-lysinamidomethyl)3-chloro-4,5-dihydroisoxazole;

5-(N-benzyloxycarbonyl-β-benzyl-L-aspartic acid-amidomethyl)-3-chloro-4,5-dihydroisoxazole;

5-(N-benzyloxycarbonyl-L-glutamic acid-amidomethyl)-3-chloro-4,5-dihydroisoxazole;

5-(N-acetyl-L-naphthylalaninamidomethyl)-3-chloro-4,5-dihydroisoxazole;

5-(N-benzyloxycarbonyl-glycinamidomethyl)-3-chloro-4,5-dihydroisoxazole;

5-(N-benzyloxycarbonyl-L-isoleucinamidomethyl)-3-chloro-4,5-dihydroisoxazole;

5-(N-[9-fluorenylmethyloxycarbonyl]-L-phenylalaninamidomethyl)3-chloro-4,5-dihydroisoxazole;

5-(N-tert-butoxycarbonyl-O-benzyl-L-threoninamidomethyl)3-chloro-4,5-dihydroisoxazole;

5-(N-benzyloxycarbonyl-L-threoninamidomethyl)-3-chloro-4,5-dihydroisoxazole;

5-(N-benzyloxycarbonyl-L-alanyl-L-phenylalaninamidomethyl)3-chloro-4,5-dihydroisoxazole;

5-(N-benzoyl-L-phenylalaninamidomethyl)-3-chloro-4,5-dihydroisoxazole;

5-(N-benzyloxycarbonyl-D-phenylalaninamidomethyl)-3-chloro-4,5-dihydroisoxazole;

5-(N-benzyloxycarbonyl-L-naphthylmethyl-glycinamidomethyl)3-chloro-4,5-dihydroisoxazole;

5-(N-benzyloxycarbonyl-L-γ-glutaminamidomethyl)-3-chloro-4,5-dihydroisoxazole;

5-(N-phthaloyl-L-phenylalaninamidomethyl)-3-chloro-4,5-dihydroisoxazole;

5-(N-benzyloxycarbonyl-D,L-meta-tyrosinamidomethyl)-3-chloro-4,5-dihydroisoxazole;

5-(N-benzyloxycarbonyl-L-meta-tyrosinamidomethyl)-3-chloro-4,5-dihydroisoxazole;

5-(N-benzyloxycarbonyl-L-2-methoxyphenylalaninamidomethyl)-3-chloro-4,5-dihydroisoxazole;

5-(N-benzyloxycarbonyl-L-3-methoxyphenylalaninamidomethyl)-3-chloro-4,5-dihydroisoxazole;

5-(N-benzyloxycarbonyl-L-4-methoxyphenylalaninamidomethyl)-3chloro-4,5-dihydroisoxazole;

5-(N-benzyloxycarbonyl-L-3,4-dihydroxyphenylalaninamidomethyl)-3-chloro-4,5-dihydroisoxazole;

5-(N-benzyloxycarbonyl-L-tryptophanamidomethyl)-3-chloro-4,5-dihydroisoxazole;

5-(N-benzyloxycarbonyl-L-5-hydroxytryptophanamidomethyl)-3-chloro-4,5-dihydroisoxazole.

5-(N-benzyloxycarbonyl-L-phenylalanyl-L-alaninamidomethyl)-3-chloro-4,5-dihydroisoxazole; and 5-(N-benzyloxycarbonyl-L-alanyl-L-phenylalaninamidomethyl)-3-bromo-4,5-dihydroisoxazole.

EXAMPLE 3 (Step G - Scheme II)

5-(N-benzyloxycarbonyl-L-phenylalaninamidomethyl)-3-bromo-4,5-dihydroisoxazole

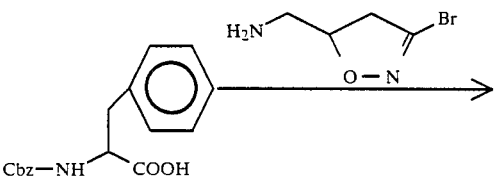

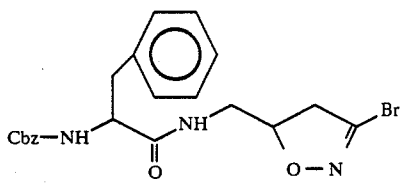

To a solution of N-benzyloxycarbonyl-L-phenylalanine, 0.84 gm, at −20° C. in 50 ml of dry CHCl₃, was added N-methyl piperidine, 0.34 ml, with stirring under argon. After 5 minutes, isobutyl chloroformate, 0.36 ml, was added dropwise and after 20 minutes, 5-aminomethyl-3-bromo-4,5-dihydroisoxazole, [optically active $[\alpha]_D^{23} = +208.6$ (CH$_2$Cl$_2$)] 0.5 gm, was added dropwise in 10 ml of dry CHCl₃. One hour after the addition, the reaction mixture was brought to room temperature and three hours later, the reaction mixture was washed with 20 ml each of 5% HCl, water, 5% NaHCO₃, brine, and dried over anh. MgSO₄ and concentrated to give a solid residue. Crystallization from CHCl₃/pentane gave the title compound identical with the most polar isomer obtained in Example 1.

In the same manner, starting with the appropriate amine or N-protected amino acid, the following compounds were made:

5-(N-benzyloxycarbonyl-L-phenylalaninamidomethyl)-3-methoxy-4,5-dihydroisoxazole;
5-(N-benzyloxycarbonyl-L-phenylalaninamidomethyl)-3-ethylthiyl-4,5-dihydroisoxazole; and
5-(N-benzyloxycarbonyl-L-tyrosinamidomethyl)-3-ethylsulfonyl-4,5-dihydroisoxazole, 87°–92° C.

Additionally, using the appropriate starting materials from Preparations 1 and 5, the following are made:
5-(N-benzyloxycarbonyl-L-para-tyrosinamidomethyl)-3-methoxy-4,5-dihydroisoxazole;
5-(N-benzyloxycarbonyl-L-ortho-tyrosinamidomethyl)-3-methoxy-4,5-dihydroisoxazole;
5-(N-benzyloxycarbonyl-D-naphthylalaninamidomethyl)-3-methoxy-4,5-dihydroisoxazole;
5-(N-benzyloxycarbonyl-D-para-chlorophenylalaninamidomethyl)3-methoxy-4,5-dihydroisoxazole;
5-(N-tert-butoxycarbonyl-L-phenylalaninamidomethyl)-3-methoxy-4,5-dihydroisoxazole;
5-(N-benzyloxycarbonyl-L-aspartic acid-amidomethyl)-3-methoxy-4,5-dihydroisoxazole;
5-(N-benzyloxycarbonyl-L-glutamic acid-amidomethyl)-3-methoxy-4,5-dihydroisoxazole;
5-(N-benzyloxycarbonyl-5-(N-ε-tert-butoxycarbonyl-L-lysinamidomethyl)3-methoxy-4,5-dihydroisoxazole;
5-(N-benzyloxycarbonyl-β-benzyl-L-aspartic acid-amidomethyl)-3-methoxy-4,5-dihydroisoxazole;
5-(N-acetyl-L-naphthylalaninamidomethyl)-3-methoxy-4,5-dihydroisoxazole;
5-(N-benzyloxycarbonyl-glycinamidomethyl)-3-methoxy-4,5-dihydroisoxazole;
5-(N-benzyloxycarbonyl-L-isoleucinamidomethyl)-3-methoxy-4,5-dihydroisoxazole;
5-(N-[9-fluorenylmethyloxycarbonyl]-L-phenylalaninamidomethyl)3-methoxy-4,5-dihydroisoxazole;
5-(N-tert-butoxycarbonyl-O-benzyl-L-threoninamidomethyl)3-methoxy-4,5-dihydroisoxazole;
5-(N-benzyloxycarbonyl-L-threoninamidomethyl)-3-methoxy-4,5-dihydroisoxazole;
5-(N-benzyloxycarbonyl-L-alanyl-L-phenylalaninamidomethyl)3-methoxy-4,5-dihydroisoxazole;
5-(N-benzoyl-L-phenylalaninamidomethyl)-3-methoxy-4,5-dihydroisoxazole;
5-(N-benzyloxycarbonyl-D-phenylalaninamidomethyl)-3-methoxy-4,5-dihydroisoxazole;
5-(N-benzyloxycarbonyl-L-naphthylmethylglycinamidomethyl)3-methoxy-4,5-dihydroisoxazole;
5-(N-benzyloxycarbonyl-L-γ-glutaminamidomethyl)-3-methoxy-4,5-dihydroisoxazole;
5-(N-phthaloyl-L-phenylalaninamidomethyl)-3-methoxy-4,5-dihydroisoxazole;
5-(N-benzyloxycarbonyl-D,L-meta-tyrosinamidomethyl)-3-methoxy-4,5-dihydroisoxazole;
5-(N-benzyloxycarbonyl-L-meta-tyrosinamidomethyl)-3-methoxy-4,5-dihydroisoxazole;
5-(N-benzyloxycarbonyl-L-2-methoxyphenylalanamidomethyl)-3-methoxy-4,5-dihydroisoxazole;
5-(N-benzyloxycarbonyl-L-3-methoxyphenylalanamidomethyl)-3-methoxy-4,5-dihydroisoxazole;
5-(N-benxyloxycarbonyl-L-4-methoxyphenylalanamidomethyl)-3-methoxy-4,5-dihydroisoxazole;
5-(N-benzyloxycarbonyl-L-3,4-dihydroxyphenylalaninamidomethyl)-3-methoxy-4,5-dihydroisoxazole;
5-(N-benzyloxycarbonyl-L-tryptophanamidomethyl)-3-methoxy-4,5-dihydroisoxazole;
5-(N-benzyloxycarbonyl-L-5-hydroxytryptophanamidomethyl)-3-methoxy-4,5-dihydroisoxazole;
5-(N-benzyloxycarbonyl-L-phenylalanyl-L-alaninamidomethyl)-3-methoxy-4,5-dihydroisoxazole;
5-(N-benzyloxycarbonyl-L-alanyl-L-phenylalaninamidomethyl)-3-methoxy-4,5-dihydroisoxazole;
5-(N-benzyloxycarbonyl-L-phenylalaninamidomethyl)-3-ethylthiyl-4,5-dihydroisoxazole;
5-(N-benzyloxycarbonyl-L-para-tyrosinamidomethyl)-3-ethylthiyl-4,5-dihydroisoxazole;
5-(N-benzyloxycarbonyl-L-ortho-tyrosinamidomethyl)-3-ethylthiyl-4,5-dihydroisoxazole;
5-(N-benzyloxycarbonyl-D-naphthylalaninamidomethyl)-3-ethylthiyl-4,5-dihydroisoxazole;
5-(N-benzyloxycarbonyl-D-para-chlorophenylalaninamidomethyl)3-ethylthiyl-4,5-dihydroisoxazole;
5-(N-tert-butoxycarbonyl-L-phenylalaninamidomethyl)-3-ethylthiyl-4,5-dihydroisoxazole;
5-(N-benzyloxycarbonyl-L-aspartic acid-amidomethyl)-3-ethylthiyl-4,5-dihydroisoxazole;
5-(N-benzyloxycarbonyl-L-glutamic acid-aminomethyl)-3-ethylthiyl-4,5-dihydroisoxazole;
5-(N-benzyloxycarbonyl-5-(N-ε-tert-butoxycarbonyl-L-lysinamidomethyl)3-ethylthiyl-4,5-dihydroisoxazole;
5-(N-benzyloxycarbonyl-β-benzyl-L-aspartic acid-amidomethyl)-3-ethylthiyl-4,5-dihydroisoxazole;
5-(N-acetyl-L-naphthylalaninamidomethyl)-3-ethylthiyl-4,5-dihydroisoxazole;
5-(N-benzyloxycarbonyl-glycinamidomethyl)-3-ethylthiyl-4,5-dihydroisoxazole;

5-(N-benzyloxycarbonyl-L-isoleucinamidomethyl)-3-ethylthiyl-4,5-dihydroisoxazole;

5-(N-[9-fluorenylmethyloxycarbonyl]-L-phenylalaninamidomethyl)3-ethylthiyl-4,5-dihydroisoxazole;

5-(N-tert-butoxycarbonyl-O-benzyl-L-threoninamidomethyl)3-ethylthiyl-4,5-dihydroisoxazole;

5-(N-benzyloxycarbonyl-L-threoninamidomethyl)-3-ethylthiyl-4,5-dihydroisoxazole;

5-(N-benzyloxycarbonyl-L-alanyl-L-phenylalaninamidomethyl)3-ethylthiyl-4,5-dihydroisoxazole;

5-(N-benzoyl-L-phenylalaninamidomethyl)-3-ethylthiyl-4,5-dihydroisoxazole;

5-(N-benzyloxycarbonyl-D-phenylalaninamidomethyl)-3-ethylthiyl-4,5-dihydroisoxazole;

5-(N-benzyloxycarbonyl-L-naphthylmethylglycinamidomethyl)3-ethylthiyl-4,5-dihydroisoxazole;

5-(N-benzyloxycarbonyl-L-γ-glutaminamidomethyl)-3-ethylthiyl-4,5-dihydroisoxazole;

5-(N-phthaloyl-L-phenylalaninamidomethyl)-3-ethylthiyl-4,5-dihydroisoxazole;

5-(N-benzyloxycarbonyl-D,L-meta-tyrosinamidomethyl)-3-ethylthiyl-4,5-dihydroisoxazole;

5-(N-benzyloxycarbonyl-L-meta-tyrosinamidomethyl)-3-ethylthiyl-4,5-dihydroisoxazole; 5-(N-benzyloxycarbonyl-L-2-methoxyphenylalanamidomethyl)-3-ethylthiyl-4,5-dihydroisoxazole;

5-(N-benzyloxycarbonyl-L-3-methoxyphenylalanamidomethyl)-3-ethylthiyl-4,5-dihydroisoxazole;

5-(N-benzyloxycarbonyl-L-4-methoxyphenylalanamidomethyl)-3-ethylthiyl-4,5-dihydroisoxazole;

5-(N-benzyloxycarbonyl-L-3,4-dihydroxyphenylalaninamidomethyl)-3-ethylthiyl-4,5-dihydroisoxazole;

5-(N-benzyloxycarbonyl-L-tryptophanamidomethyl)-3-ethylthiyl-4,5-dihydroisoxazole;

5-(N-benzyloxycarbonyl-L-5-hydroxytryptophanamidoethylthiyl)-3-methoxy-4,5-dihydroisoxazole;

5-(N-benzyloxycarbonyl-L-phenylalanyl-L-alaninamidomethyl)-3-ethylthiyl-4,5-dihydroisoxazole;

5-(N-benzyloxycarbonyl-L-alanyl-L-phenylalaninamidomethyl)-3-ethylthiyl-4,5-dihydroisoxazole;

5-(N-benzyloxycarbonyl-L-histidinamidomethyl-3-bromo-4,5-dihydroisoxaxole, 148°–154° C.;

5-(N-im-benzoyl-N-α-benzyloxycarbonyl-L-histidinamidomethyl)-3-bromo-4,5-dihydroisoxazole, 145°–152° C.;

5-(N-toluenesulfonyl glycinamidomethyl)-3-bromo-4,5-dihydroisoxazole, 151°–152° C.;

5-[N-(4-benzylcarbamoyl-L-phenylalaninamidomethyl]-3-bromo-4,5-dihydroisoxazole, 170°–175° C.;

5-[N-benzyloxycarbonyl-4-(R)-hydroxy-L-prolinamidomethyl]-3-bromo-4,5-dihydroisoxazole, 129°–136° C.;

5-(N-benzyloxycarbonyl-L-para-methoxy-L-phenylalaninamidomethyl)-3-bromo-4,5-dihydroisoxazole, 143°–145° C.;

5-(N$^\alpha$,O-dibenzyloxycarbonyl-L-5-hydroxytryptophanamidomethyl)-3-bromo-4,5-dihydroisoxazole, 152°–158° C.;

5-(N-benzyloxycarbonyl-L-tryptophanamidomethyl)-3-bromo-4,5-dihydroisoxazole, 142°–145° C.;

5-[N,O,O-tribenzyloxycarbonyl-(±)-3,4-dihydroxyphenylalaninamidomethyl]-3-bromo-4,5-dihydroisoxazole, 116°–119° C.;

5-[N-benzyloxycarbonyl-(±)-3,4-dihydroxyphenylalaninamidomethyl]-3-bromo-4,5-dihydroisoxazole, 149°–151° C.;

5-(N-benzyloxycarbonyl-L-5-hydroxy-tryptophanamidomethyl)-3-bromo-4,5-dihydroisoxazole, 78°–84° C.;

5-[N-benzyloxycarbonyl-(±)-para-fluorophenylalaninamidomethyl]-3-bromo-4,5-dihydroisoxazole, 137°–139° C.;

5-(N-tert-butoxycarbonyl-L-phenylalanyl-L-tyrosinamidomethyl)-3-bromo-4,5-dihydroisoxazole, 203°–205° C.;

5-(N$^\alpha$,N-dibenzyloxycarbonyl-L-4-aminophenylalaninamidomethyl)3-bromo-4,5-dihydroisoxazole, 201°–204° C.;

5-(N$^\alpha$-benzyloxycarbonyl-N$^{in}$-formyl-L-tryptophanamidomethyl)-3-bromo-4,5-dihydroisoxazole, 52°–66° C.;

5-(N-benzyloxycarbonyl-para-aminophenylalaninamidomethyl)-3-bromo-4,5-dihydroisoxazole, 149°–153° C.;

5-(L-phenylalanyl-L-tyrosinamidomethyl)-3-bromo-4,5-dihydroisoxazole-para-toluene-sulfonic acid, 193°–199° C. (dec);

5-(N-benzyloxycarbonyl-S-benzyl-L-cysteinamidomethyl)-3-bromo-4,5-dihydroisoxazole, 75°–77° C.;

5-(N-benzyloxycarbonyl-L-methioninamidomethyl)-3-bromo-4,5-dihydroisoxazole, 130°–133° C.;

5-(N-benzyloxycarbonyl-O-acetyl-L-tyrosinamidomethyl)-5-(S)-3-bromo-4,5-dihydroisoxazole, 152°–154° C., [α]D = +35;

5-(N,O-dibenzyloxycarbonyl-3-methoxy-L-tyrosinamidomethyl)-3-bromo-4,5-dihydroisoxazole, 169°–172° C.;

5-(N-benzyloxycarbonyl-3-methoxy-L-tyrosinamidomethyl)-3-bromo-4,5-dihydroisoxazole, 144°–145° C.;

5-(N-benzyloxycarbonyl-(±)-para-iodo-phenylalaninamidomethyl)-3-bromo-4,5-dihydroisoxazole, 154°–156° C.; and 5-[N-2-(S)-(6-methoxy-2-naphthyl)-propionyl-L-tyrosinamidomethyl]-5-(S)-3-bromo-4,5-dihydroisoxazole.

EXAMPLE 4 (Step G - Scheme II)

5-(N-benzyloxycarbonyl-L-tyrosinamidomethyl)-3-chloro-4,5-dihydroisoxazole

The 5-aminomethyl-3-chloro-4,5-dihydroisoxazole hydrochloride salt of Preparation 7 (2.9 gm., 17 mmol) was placed in a 500 mL beaker with stirring bar, and dissolved in 60 mL of water. Methylene chloride (80 mL) was added and the vigorously stirred two-phase mixture was treated with Na$_2$CO$_3$ to a pH of 9–10. The mixture was transferred to a separatory funnel and the CH$_2$Cl$_2$ phase was collected. The aqueous phase was saturated with NaCl and washed four times with equal volumes of CH$_2$Cl$_2$. The organic phase was combined and washed with brine, dried (MgSO$_4$), filtered and condensed to give 2.16 gm of the free amine as a light yellow mobile oil.

The oil was dissolved in EtOAc and transferred to a dry 500 mL round bottom flask fitted with drying tube and thermometer and containing N-carbobenzyloxy-L-tyrosine (5.04 gm, Sigma). Ethyl acetate (total volume approximatly 300 mL) was added and the flask cooled to 0° C. (ice & NaCl). Then a mixture of 1-(3-dimethylaminopropyl)-3-ethyl-carbodiimide hydrochloride (3.7 gm) and 4-dimethylaminopyridine (390 mg) was added portion-wise over 0.5 hr. The mixture was left to slowly warm to room temperature over several hours. The mixture was then transferred to a separatory funnel and washed with 200 mL each of 5% HCl, 5% NaHCO$_3$, brine and dried (MgSO$_4$), filtered and condensed to give a solid residue. Purification by column chromatography on silica gel (40–60% EtOAc/petroleum ether) gave the coupled amide product as a semi-crystalline foam. Crystallization from EtOAc/petroleum ether gives the product as a gel-like material requiring evacuation to remove traces of solvent.

Similarly, the following compounds were prepared:
5-(N-α-benzyloxycarbonyl-L-glutamatamidomethyl)-3-chloro-4,5-dihydroisoxazole, 54°–62°;
5-(N-para-methoxybenzyloxycarbonyl-L-tyrosinamidomethyl)-5-(S)-3-chloro-4,5-dihydroisoxazole, 148°–149° C.;
5-[N-[2-(S)-(6-methoxy-2 naphthyl)-propionyl]-L-tyrosinamidomethyl] 5-(S)-3-chloro-4,5-dihydroisoxazole, 215°–216° C., [α]D= +33.0°;
5-[N-(2-naphthyl-acetyl)-L-tyrosinamidomethyl]-5-(S)-3-chloro-4,5-dihydroisoxazole, 151°–157° C., [α]D= +46.1°; and
5-[N-(1-Naphthyl-acetyl)-L-tyrosinamidomethyl]-5-(S)-3-chloro-4,5-dihydroisoxazole, 215°–217° C., [α]D= +67.2°.

EXAMPLE 5 (Step H - Scheme III)

5-(L-phenylalaninamidomethyl)-3-bromo-4,5-dihydroisoxazole trifluoroacetate acid salt

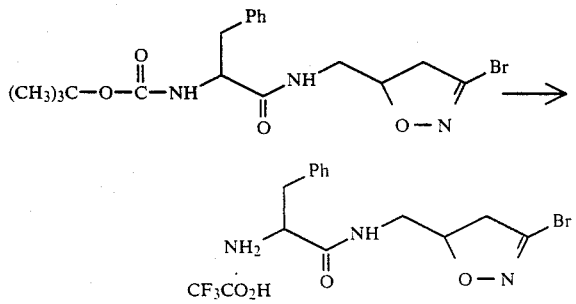

5-(N-tert-butoxycarbonyl-L-phenylalaninamidomethyl)-3-bromo-4,5-dihydroisoxazole, 7 gm, was taken in 100 ml of 20% CF$_3$CO$_2$H/CH$_2$Cl$_2$ at 0° C. for 24 hrs. Concentration gave an oily foamy substance. $^1$H NMR [80 MHz, CDCl$_3$(H$_2$O)]; delta 2.8–3.5 (m, 4H, CH$_2$), 4.2–4.9 (m, 2H, CH), 4.7 (s, HOD), 7.3 ppm (s, 5H, pH).

EXAMPLE 6 (Step I - Scheme III)

5-(N-tert-butoxycarbonyl-glycyl-L-phenylalaninamidomethyl-3-bromo-4,5-dihydroisoxazole To a 175 mg of N-tertbutoxycarbonyl glycine in 200 ml of EtOAc at 0° C. were added 400 mg of 5-(L-phenylalaninamidomethyl)-3-bromo-4,5-dihydroisoxazole trifluoroacetic acid salt, followed by 0.15 ml of NEt$_3$, 120 mg of DMAP and 300 mg of EDCI. The reaction mixture was brought to room temperature and after 16 hrs, it was washed with water, 5% HCl, water, 5% NaHCO$_3$, brine, dried over anhydrous MgSO$_4$ and concentrated to give a semi-solid material. Crystallization took place from ethylacetate, hexane to give product, melting point, 162°–169° C.(dec). $^1$H NMR (80 MHz, CDCl$_3$); delta 1.45 (s, 9H, (CH$_3$)$_3$C), 2.8–3.3 (m, 4H, CH$_2$), 3.45 (t, 2H, CH$_2$), 3.75 (d, 2H, CH$_2$), 4.5–4.9 (m, 2H, CH), 5.1 (broad t, 1H, NH), 6.6 (broad, 2H, NH), 7.3 ppm (s, 5H, Ph).

Similarly, the following compounds were prepared:
5-(N-isobutyloxycarbonyl-L-phenylalaninamidomethyl)-3-bromo-4,5-dihydroisoxazole;
5-(N-succinyl-L-phenylalaninamidomethyl)-3-bromo-4,5-dihydroisoxazole; 85°–97° C.;
5-(N-benzyloxycarbonyl-L-threonyl-L-phenylalaninamidomethyl)-3-bromo-4,5-dihydroisoxazole, 108°–117° C.;
5-[N-cinnamoyl-L-phenylalaninamidomethyl)-3-bromo-4,5-dihydroisoxazole;
5-[N-(2(S)-6-methoxy-2-naphthylpropionyl)-L-phenylalaninamidomethyl]-3-bromo-4,5-dihydroisoxazole;
5-[N-(2(S)-6-methoxy-2-naphthylpropionyl)-L-phenylalaninamidomethyl]-5-(R)-3-bromo-4,5-dihydroisoxazole;
5-[N-(2-(S)-6-methoxy-2-naphthylpropionyl)-L-phenylalaninamidomethyl]-5-(S)-3-bromo-4,5-dihydroisoxazole;
5-(N-adamantyloxycarbonyl-L-phenylalaninamidomethyl)-3-bromo-4,5-dihydroisoxazole, 114°–117° C. (dec);
5-(N-chlorobenzyloxycarbonyl-L-phenylalaninamidomethyl)-3-bromo-4,5-dihydroisoxazole, 91°–93° C.;
5-[N-(4-methoxybenzyloxycarbonyl)-L-phenylalaninamidomethyl]-3-bromo-4,5-dihydroisoxazole;
5-[N-(4-methoxybenzyloxycarbonyl)-L-phenylalaninamidomethyl]-5-(R)-3-bromo-4,5-dihydroisoxazole;
5-[N-(4-methoxybenzyloxycarbonyl)-L-phenylalaninamidomethyl]-5-(S)-3-bromo-4,5-dihydroisoxazole;
5-(N-tertbutoxycarbonyl-glycyl-L-phenylalaninamidomethyl)-3-bromo-4,5-dihydroisoxazole, 162°–169° C. (dec);
5-(N-(6-methoxynaphthylacetyl)-L-phenylalaninamidomethyl)-5-(S)-3-chloro-4,5-dihydroisoxazole; and
5-(N-(6-methoxynaphthylacetyl)-L-tyrosinamidomethyl)-5-(S)-3-chloro-4,5-dihydroisoxazole.

EXAMPLE 7

5-(N-tert-butoxycarbonyl-amidomethyl)-3ethylsulfonyl-4,5-dihydroisoxazole

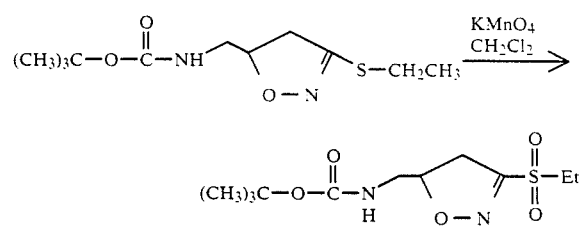

To a solution of 5-(N-tert-butoxycarbonylaminomethyl)-3-ethylthiyl-4,5-dihydroisoxazole, 180 mg, in 8 ml. of CH$_2$Cl$_2$ was added dropwise. 195 mg of KMnO$_4$ dissolved in 10 ml of water. The mixture was stirred for about 10 hours and filtered through a plug of celite. The filtrate was then transferred to a separatory funnel and the methylene chloride layer was washed successively with water and then brine, dried (MgSO$_4$), filtered and concentrated to give 114 mg of a viscous oil.

IR (neat): 3370, 2980, 1710, 1515, 1168 cm$^{-1}$. $^1$H NMR (80 MHz, CDCl$_3$) delta 4.70–5.41 (m, 1H, NH), 4.47–4.91 (m, 1H, CHO), 3.3–3.65 (m, 2H, C$\underline{H_2}$NH), 2.82–3.63 (m, 2H, S—C$\underline{H_2}$), 2.49–3.61 (m, 2H, C$\underline{H_2}$CHO), 1.52–1.07 (m, 3$\overline{H}$, CH$_2$—C$\underline{H_3}$). 1.42 (s, 9H, —C(C$\underline{H_3}$)$_3$).

EXAMPLE 8

5-(N-α-benzyloxycarbonyl-1-L-lysinamidomethyl)-3-bromo-4,5-dihydroisoxazole-oxalic acid

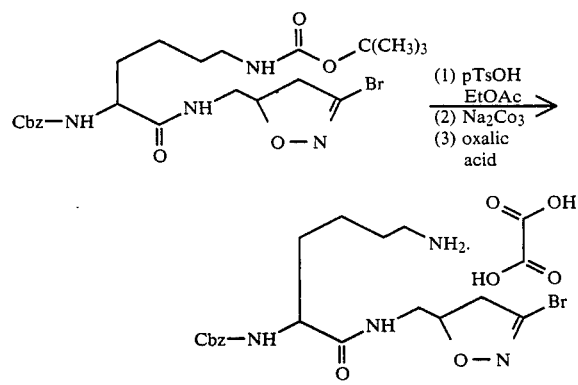

To a solution of 5-(N-benzyloxycarbonyl-N-ε-tert-butoxycarbonyl-L-lysine-amidomethyl)-3-bromo-4,5-dihydroisoxazole, 150 mg, in 25 mL of ethyl acetate was added 53 mg. of para-toluene sulfonic acid monohydrate. The mixture was stirred overnight and the solid material collected by filtration. This material was then taken up in 15 ml of water and transferred to a beaker containing 20 mL of CH$_2$Cl$_2$. With rapid stirring an amount of solid Na$_2$CO$_3$ was added to obtain a pH of 9. After about 0.5 hr the mixture was transferred to a separatory funnel and the methylene chloride layer was collected. The basic phase was extracted twice (2×20 mL CH$_2$Cl$_2$) and the combined organic phase was washed with brine, dried (MgSO$_4$), filtered and concentrated to provide 117 mg of a viscous oil. The oil was subsequently taken up in about 15 mL of ether and treated with 24 mg. of oxalic acid. The solid material was collected by filtration and further purified by crystallization from methanol/ethyl acetate solution providing 56 mg. of the product, m.p=96°–108° C. IR (KBr): 3322, 1720, 1650, 1530, 1236 cm$^{-1}$. $^1$H NMR (80 MHz, D$_2$O) delta 7.51 (s, 5H, pH), 5.12 (s, 2H, PhCH$_2$O), 4.50–4.91 (m, 1H, CHO), 3.79–4.22 (m, 1H, C$\underline{H}$N), 3.27–3.65 (m, 2H, C$\underline{H_2}$NH), 2.68–3.26 (m, 4H, C$\underline{H_2}$CHO+C$\underline{H_2}$—NH$_2$), 1.21–1.89 (6H, —(C$\underline{H_2}$)$_3$—CH).

In a similar manner, 5-(glycyl-L-phenylalaninamidomethyl) -3-bromo-4,5-dihydroisoxazole oxalate salt, m.p. 135°–140° C., was made.

EXAMPLE 9

Topical Formulation

| Ingredients | wt % |
|---|---|
| Active compound | 2.5 |
| Klucel (hydroxypropylcellulose) | 2.5 |
| diisopropyl adipate | 10 |
| ethanol | 80 |
| propylene glycol | 5 |

All of the ingredients except Klucel are first mixed together at room temperature, so that the active compuond dissolves. Then the Klucel is dispersed and left to gel overnight.

EXAMPLE 10

Mexican Hairless Dog Assays

A gel consisting of 2.5% of 5-(N-benzyloxycarbonyl-L-phenylalaninamidomethyl)-3-bromo-4,5-dihydroisoxazole (mixture of diastereomers), 2.5% Klucel, 10% diisopropyl adipate, 80% ethanol and 5% propylene glycol applied once daily to two dogs for 14 days resulted in clearing of the majority of blackhead-like lesions and many whitehead-like lesions. 5-(N-benzyloxycarbonyl-L-phenylalaninamidomethyl)-3-chloro-4,5-dihydroisoxazole (mixture of diastereomers) (2.5%) in an identical gel also showed good clearing when applied to two dogs once daily for 14 days. In all cases gel vehicle alone did not result in significant clearing.

A gel consisting of either 2.5% 5-(N-benzyloxycarbonyl-L-phenylalaninamidomethyl)-3-bromo-4,5-dihydroisoxazole (mixture of diastereomers), 2.5% 5-(N-benzyloxycarbonyl-L-phenylalaninamidomethyl)-3-chloro-4,5-dihydroisoxazole (mixture of diastereomers) or 2.5% 5-(N-benzyloxycarbonyl-L-paratyrosinamidomethyl)-3-bromo-4,5-dihydroisoxazole (mixture of diastereomers), and 40% dimethylisosorbidem 55% ethanol, and 2.5% carbomer 940, also showed positive results in two dogs. One dog showed partial clearing of lesions, and the other dog showed clearing in the majority of lesions. Gel vehicle alone was not effective.

EXAMPLE 11

Rodent Ear Assays

The following compounds of this invention were applied topically in vivo to the skin of the ears and backs of rodents in several assays:
5-(N-benzyloxycarbonyl-L-phenylalaninamidomethyl)-3-bromo-4,5-dihydroisoxazole (mixture of diastereomers);
5-(N-benzyloxycarbonyl-L-phenylalaninamidomethyl)-3-chloro-4,5-dihydroisoxazole (mixture of diastereomers);
5-(N-benzyloxycarbonyl-L-paratyrosinamidomethyl)-3-bromo-4,5-dihydroisoxazole (mixture of diastereomers);
5-(N-benzyloxycarbonyl-L-phenylalaninamidomethyl)-3-bromo-4,5-dihydroisoxazole (more polar diastereomer); and
5-(N-benzyloxycarbonyl-L-phenylalaninamidomethyl)-3-bromo-4,5-dihydroisoxazole (less polar diastereomer).

The compounds were applied in acetone in 5% (w/v) concentration. The epidermis was harvested and transglutaminase activity determined according to accepted procedures described in the literature (see, De Young and Ballaron, J. of Invest. Dermatology 79, (1982)). All of the tested compounds except the less polar diastereomer exhibited inhibition of transglutaminase activity ranging from 70-95%.

EXAMPLE 12

Toxicity of the Compounds of Formula I

Three groups, each composed of 5 male and 5 female CDI mice, were injected intraperitoneally with 10 mg/Kg of 5-(N-benzyloxycarbonyl-L-phenylalaninamidomethyl)-3-bromo-4,5-dihydroisoxazole or 5-(N-benzyloxycarbonyl-L-para-tyrosinamidomethyl)-3-chloro-4,5-dihydroisoxazole daily for 14 days. No toxic effects were noted.

Other compounds of Formula I also do not exhibit any toxic effects.

EXAMPLE 13

5-(N-benzyloxycarbonyl-L-phenylalaninamidomethyl)-3-bromo-4,5-dihydroisoxazole was levigated into a gel vehicle (see Example 14) to afford a concentration of 1% w/w. The gel vehicle contained primarily propylene glycol which was gelled with Carbopol 940.

0.05 ml of the gel containing active ingredient was filled into a 1 mm deep teflon chamber (Durhing chamber) which was then applied to the psoriatic plaque of each of the five subjects. The plaque was then covered with Scanpor* adhesive tape. The gel was applied on days 1, 3, 5, 8, 10, 12 and 16. Each time, fresh gel, chamber, and tape were used. Readings were taken on Days 5, 10, 12, 16 and 23 (one week off therapy). The presence or absence of a normal appearing epidermis was evaluated using a scale of 0 to 2. The compound tested shows activity against psoriasis.

EXAMPLE 14

Formulation

| Ingredients | wt % |
| --- | --- |
| Purified water U.S.P. | 3 |
| Carbopol 940 | 2 |
| Propyl gallate | 0.01 |
| Edetate disodium, U.S.P. | 0.01 |
| Propylene glycol, U.S.P. q.s. to | 100 ml |
| 5-(N-benzyloxycarbonyl-L-phenylalanin amidomethyl)-3-bromo-4,5-dihydroisoxazole | 1% |

All ingredients except the drug were formulated into a placebo; then 0.2 g of drug were levigated into 19.8 g of placebo gel.

What is claimed is:

1. A method for treating mammals which have a disease stated characterized by elevated transglutaminsase activity comprising administering to the mammals a therapeutically effective amount of a compound of the formula;

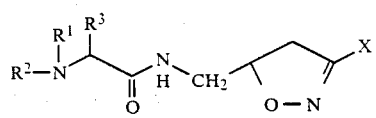

or an optical isomer thereof, or a pharmaceutically acceptable salt thereof, wherein:

$R^1$ and $R^2$, together with the nitrogen atom to which they are attached, represent phthalimido; or $R^1$ and $R^3$ together form —CH$_2$—CH$_2$—CH$_2$— or CH$_2$—CHOH—CH$_2$; or $R^1$, $R^2$ and $R^3$ are defined as follows:

$R^1$ is hydrogen or methyl;
$R^2$ is selected from the group consisting of:
(1) hydrogen;
(2) alkyl;
(3) lower alkyl sulfonyl;
(4) aryl sulfonyl;
(5) aryl sulfonyl substituted with lower alkyl on the aryl moiety;
(6) 9-fluorenylmethyloxycarbonyl, succinyl or cinnamoyl;
(7) a radical of the formula:

wherein:

$R^9$ is hydrogen; alkyl of 1 to 4 carbon atoms; aryl; aryl substituted with up to 2 substituents where the substituents are independently halo, lower alkyl, alkoxy, nitro, trifluoromethyl, carboxyl, or alkoxycarbonyl; aralkyl; pyridinyl; furanyl; alkoxy; aralkoxy; aralkoxy substituted on the aryl radical with up to 2 substituents where the substituents are independently halo, lower alkyl, alkoxy, nitro, or trifluoromethyl; adamantyloxy; aralkylamino; or aralkyl substituted on the aryl radical with up to 2 substituents where the substituents are independently hydroxy, alkoxy or halo; and (8) a radical of the formula:

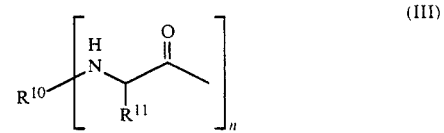

wherein:

n = 0 or 1;
$R^{10}$ is independently hydrogen, alkyl or the radical defined by formula (II) above;
$R^{11}$ is selected from the group consisting of: hydrogen; lower alkyl; —(CHR$^{12}$)$_m$WR$^{13}$ wherein m is 1 or 2, W is oxygen or sulfur and $R^{12}$ and $R^{13}$ are independently hydrogen or methyl; —CH(CH$_3$)—OCH$_2$C$_6$H$_5$;
—(CH$_2$)$_k$C(O)Y wherein k is 1 or 2 and Y is hydroxy, amino, alkoxy, or aralkoxy;
—(CH$_2$)$_p$NHCH(NHR$^{14}$)NR$^{15}$ wherein p is 2,3, or 4 and $R^{14}$ and $R^{15}$ are independently hydrogen or lower alkyl;
—(CH$_2$)$_q$NH$_2$ wherein q is 2, 3, 4, or 5;
—(CH$_2$)$_4$NHCOOC(CH$_3$)$_3$;
—(CH$_2$)$_2$CHOHCH$_2$NH$_2$; a radical of formula:

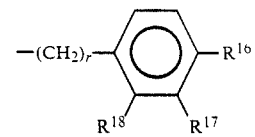

wherein r is 1 or 2 and $R^{16}$, $R^{17}$ and $R^{18}$ are independently hydrogen, hydroxy, halo, methoxy, lower alkyl, halo lower alkyl, amino, N-protected amino, guanidino, nitro cyano, —COOH, —CONH$_2$, —COOR''' where R''' is lower alkyl, or —OR* where R* is an O-protecting group; and a radical chosen from

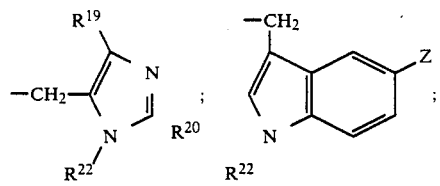

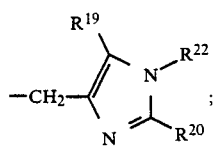

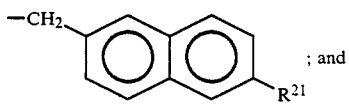; and

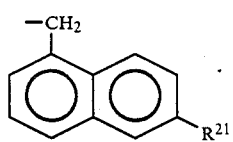

wherein $R^{19}$ and $R^{20}$ are independently hydrogen, lower alkyl, halo or trifluoromethyl alkyl; $R^{21}$ is hydrogen, hydroxy or methoxy; and Z is hydrogen, hydroxy, or —OR* where R* is an O-protecting group; $R^{22}$ is hydrogen or an N-protecting group for imidazole or indole functionalities; $R^3$ is independently selected from the group recited for $R^{11}$ above; and X is selected from the group consisting of: halo; —OR, —SR, —S(O)R, —S(O$_2$)R, —S(O)$_2$NH$_2$ or —S(O)$_2$NHR wherein R is lower alkyl, mono-, di- or tri-fluoro alkyl of 2 or 3 carbon atoms, aryl, or optionally substituted aryl; —NR'R" wherein R' and R" are independently hydrogen, lower alkyl, or aryl; and

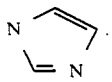

2. A method according to claim 1 wherein said mammal is a human and said disease state is acne.

3. A method according to claim 1 wherein said mammal is a human and said disease state is psoriasis.

4. A method according to claim 1 wherein said mammal is a human and said disease state is cataracts.

5. A method for treating mammals which have a disease state characterized by elevated transglutaminase activity comprising administering to the mammal a thereapeutically effective amount of a compound of the formula:

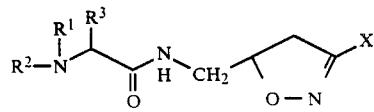 (I)

or an optical isomer thereof, or a pharmaceutically acceptable salt thereof, wherein:
$R^1$ and $R^2$, together with the nitrogen atom to which they are attached, represent phthalimido; or $R^1$, $R^2$ and $R^3$ are defined as follows:
$R^1$ is hydrogen;
$R^2$ is selected from the group consisting of:
aryl sulfonyl substituted with lower alkyl on the aryl moiety;
9-fluorenylmethyloxycarbonyl;
succinyl;
cinnamoyl; and
a radical of the formula:

 (II)

wherein:
$R^9$ is hydrogen, alkyl of 1 to 4 carbon atoms; aryl with up to 2 substituents where the substituents are independently halo, lower alkyl or alkoxy; aralkyl; aralkoxy; aralkoxy substituted on the aryl radical with up to 2 substituents where the substituents are independently halo, lower alkyl, or lower alkoxy; adamantyloxy; and a radical of the formula:

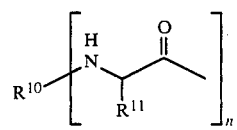 (III)

wherein:
n=0 or 1;
$R^{10}$ is independently hydrogen, alkyl or the radical defined by formula (II) above;
$R^{11}$ is selected from the group consisting of:
hydrogen; lower alkyl; —(CHR$^{12}$)$_m$WR$^{13}$ wherein m is 1 or 2, W is oxygen or sulfur and $R^{12}$ and $R^{13}$ are independently hydrogen or methyl;
—(CH$_2$)$_k$C(O)Y wherein k is 1 or 2 and Y is hydroxy or amino, —(CH$_2$)$_p$NHCH(NHR$^{14}$)NR$^{15}$ wherein p is 2,3, or 4 and $R^{14}$ and $R^{15}$ are independently hydrogen;
—(CH$_2$)$_q$NH$_2$ wherein q is 2, 3, 4, or 5;
a radical of formula:

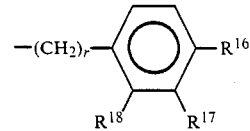

wherein:
r is 1 and $R^{16}$, $R^{17}$ and $R^{18}$ are independently hydrogen, hydroxy, halo, methoxy, or amino, and a radical chosen from:

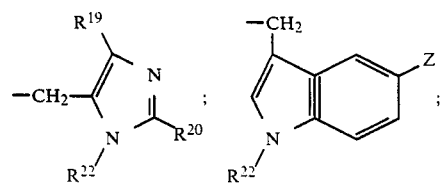

-continued

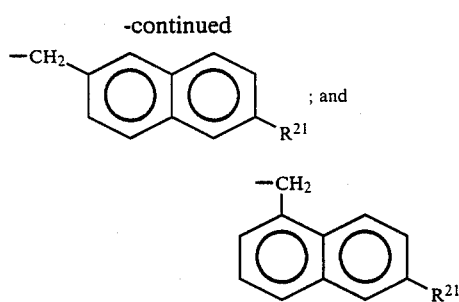

wherein:
R[19] and R[20] are independently hydrogen, R[21] is hydrogen, hydroxy or methoxy; and Z is hydrogen, hydroxy, or —OR* where R* is an O-protecting group;
R[22] is hydrogen or an N-protecting group for imidazole or indole functionalities;
R[3] is independently selected from the group recited for R[11] above; and
X is selected from the group consisting of chloro and bromo.

6. A method for treating a hyman having a disease state characterized by elevated transglutaminase activity comprising administering to the human a therapeutically effective amount of a compound, or an optical isomer thereof, selected from the group consisting of:

5-(N-benzyloxycarbonyl-L-phenylalaninamidomethyl)-3-chloro-4,5-dihydroisoxazole;
5-(N-benzyloxycarbonyl-L-phenylalaninamidomethyl)-3-bromo-4,5-dihydroisoxazole;
5-(N-benzyloxycarbonyl-L-para-tyrosinamidomethyl)-3-bromo-4,5-dihydroisoxazole;
5-(N-benzyloxycarbonyl-L-ortho-tyrosinamidomethyl)-3-bromo-4,5-dihydroisoxazole;
5-(N-benzyloxycarbonyl-D-naphthylalaninamidomethyl)-3-chloro-4,5-dihydroisoxazole;
5-(N-benzyloxycarbonyl-D-para-chlorophenylalaninamidomethyl)-3-chloro-4,5-dihydroisoxazole;
5-(N-tert-butoxycarbonyl-L-phenylalaninamidomethyl)-3-bromo-4,5-dihydroisoxazole;
5-(N-benzyloxycarbonyl-L-aspartic acid-α-amidomethyl)-3-bromo-4,5-dihydroisoxazole;
5-(N-benzyloxycarbonyl-N-ε-tert-butoxycarbonyl-L-lysine-amidomethyl)-3-bromo-4,5-dihydroisoxazole;
5-(N-benzyloxycarbonyl-β-benzyl-L-aspartic acid amidomethyl)-3-bromo-4,5-dihydroisoxazole;
5-(N-benzyloxycarbonyl-L-glutamic acid amidomethyl)-3-bromo-4,5-dihydroisoxazole;
5-(N-benzyloxycarbonyl-β-benzyl-L-aspartic acid amidomethyl)-3-chloro-4,5-dihydroisoxazole;
5-(N-acetyl-L-naphthylalaninamidomethyl)-3-bromo-4,5-diihydroisoxazole;
5-(N-benzyloxycarbonyl-glycinamidomethyl)-3-bromo-4,5-dihydroisoxazole;
5-(N-benzyloxycarbonyl-L-isoleucinamidomethyl)-3-bromo-4,5-dihydroisoxazole;
5-(N-(9-fluorenylmethyloxycarbonyl)-L-phenylalaninamidomethyl)-3-bromo-4,5-dihydroisoxazole;
5-(N-tert-butoxycarbonyl-O-benzyl-L-threoninamidomethyl)-3-bromo-4,5-dihydroisoxazole;
5-(N-benzyloxycarbonyl-L-threoninamidomethyl)-3-bromo-4,5-dihydroisoxazole;
5-(N-benzyloxycarbonyl-L-phenylalaninyl-L-alaninamidomethyl)-3-bromo-4,5-dihydroisoxazole;
5-(N-benzyloxycarbonyl-L-alanyl-L-phenylalaninamidomethyl)-3-bromo-4,5-dihydroisoxazole;
5-(N-benzoyl-L-phenylalaninamidomethyl)-3-bromo-4,5-dihydroisoxazole;
5-(N-benzyloxycarbonyl-D-phenylalaninamidomethyl)-3-bromo-4,5-dihydroisoxazole;
5-(N-benzyloxycarbonyl-L-naphthylmethyl-glycinamidomethyl)-3-bromo-4,5-dihydroisoxazole;
5-(N-benzyloxycarbonyl-L-γ-glutamine amidomethyl)-3-bromo-4,5-dihydroisoxazole;
5-(N-phthaloyl-L-phenylalaninamidomethyl)-3-bromo-4,5-dihydroisoxazole;
5-(N-benzyloxycarbonyl-D,L-meta-tyrosinamidomethyl)-3-bromo-4,5-dihydroisoxazole;
5-(N-benzyloxycarbonyl-L-para-tyrosinamidomethyl)-3-chloro-4,5-dihydroisoxazole;
5-(N-benzyloxycarbonyl-L-para-tyrosinamidomethyl)-5-(S)-3-chloro-4,5-dihydroisoxazole;
5-(N-benzyloxycarbonyl-L-ortho-tyrosinamidomethyl)-3-cloro-4,5-dihydroisoxazole;
5-(N-benzyloxycarbonyl-L-meta-tyrosinamidomethyl)-3-bromo-4,5-dihydroisoxazole;
5-(N-benzyloxycarbonyl-L-meta-tyrosinamidomethyl)-3-chloro-4,5-dihydroisoxazole;
5-(N-benzyloxycarbonyl-L-2-methoxyphenylalaninamidomethyl)-3-bromo-4,5-dihydroisoxazole;
5-(N-benzyloxycarbonyl-L-4-methoxyphenylalaninamidomethyl)-3-chloro-4,5-dihydroisoxazole;
5-(N-benzyloxycarbonyl-L-3-methoxyphenylalaninamidomethyl)-3-bromo-4,5-dihydroisoxazole;
5-(N-benzyloxycarbonyl-L-3-methoxyphenylalaninamidomethyl)-3-chloro-4,5-dihydroisoxazole;
5-(N-benzyloxycarbonyl-L-3,4-dihydroxyphenylalaninamidomethyl)-3-bromo-4,5-dihydroisoxazole;
5-(N-benzyloxycarbonyl-L-3,4-dihydroxyphenylalaninamidomethyl)-3-chloro-4,5-dihydroisoxazole;
5-(N-benzyloxycarbonyl-L-3-methoxytyrosinamidomethyl)-3-bromo-4,5-dihydroisoxazole;
5-(N-benzyloxycarbonyl-L-3-methoxytyrosinamidomethyl)-3-chloro-4,5-dihydroisoxazole;
5-(N-benzyloxycarbonyl-L-tryptophanamidomethyl)-3-bromo-4,5-dihydroisoxazole;
5-(N-benzyloxycarbonyl-L-tryptophanamidomethyl-3-chloro-4,5-dihydroisoxazole;
5-(N-benzyloxycarbonyl-L-5-hydroxytryptophanamidomethyl)-3-bromo-4,5-dihydroisoxazole;
5-(N-benzyloxycarbonyl-L-5-hydroxytryptophanamidomethyl)-3-chloro-4,5-dihydroisoxazole;
5-(N-benzyloxycarbonyl-L-histidinamidomethyl-3-bromo-4,5-dihydroisoxazole;
5-(N-im-benzoyl-N-α-benzyloxycarbonyl-L-histidinamidomethyl)-3-bromo-4,5-dihydroisoxazole;
5-(N-toluenesulfonyl glycinamidomethyl)-3-bromo-4,5-dihydroisoxazole;
5-(N-benzylcarbamoyl-L-phenylalaninamidomethyl)-3-bromo-4,5-dihydroisoxazole;
5-(N-benzyloxycarbonyl-4-(R)-hydroxyl-L-prolinamidomethyl)-3-bromo-4,5-dihydroisoxazole;

5-(N-benzyloxycarbonyl-L-para-methoxy-L-phenylalaninamidomethyl)-3-bromo-4,5-dihydroisoxazole;
5-(N$^\alpha$, O-dibenzyloxycarbonyl-L-5-hydroxytryptophanamidomethyl)-3-bromo-4,5-dihydroisoxazole;
5-(N-benzyloxycarbonyl-L-tryptophanamidomethyl)-3-bromo-4,5-dihydroisoxazole;
5-(N,O,O-tribenzyloxycarbonyl-(±)-3,4-dihydroxyphenylalaninamidomethyl)-3-bromo-4,5-dihydroisoxazole;
5-(N-benzyloxycarbonyl-(±)-3,4-dihydroxyphenylalaninamidomethyl)-3-bromo-4,5-dihydroisoxazole;
5-(N-benzyloxycarbonyl-(±)-para-fluorophenylalaninamidomethyl)-3-bromo-4,5-dihydroisoxazole;
5-(N-tert-butoxycarbonyl-L-phenylalanyl-L-tyrosinamidomethyl)-3-bromo-4,5-dihydroisoxazole;
5-(N$^\alpha$,N-dibenzyloxycarbonyl-L-4-aminophenylalaninamidomethyl)-3-bromo-4,5-dihydroisoxazole;
5-(N$^\alpha$-benzyloxycarbonyl-N$^{in}$-formyl-L-tryptophanamidomethyl)-3-bromo-4,5-dihydroisoxazole;
5-(N-benzyloxycarbonyl-para-aminophenylalaninamidomethyl)-3-bromo-4,5-dihydroisoxazole;
5-(L-phenylalanyl-L-tyrosinamidomethyl)-3-bromo-4,5-dihydroisoxazole-para-toluene-sulfonic acid;
5-(N-benzyloxycarbonyl-S-benzyl-L-cysteinamidomethyl)-3-bromo-4,5-dihydroisoxazole;
5-(N-benzyloxycarbonyl-L-methioninamidomethyl)-3-bromo-4,5-dihydroisoxazole;
5-(N-benzyloxycarbonyl-O-acetyl-L-tyrosinamidomethyl)-5-(S)-3-bromo-4,5-dihydroisoxazole;
5-(N,O-dibenzyloxycarbonyl-3-methoxy-L-tyrosinamidomethyl)-3-bromo-4,5-dihydroisoxazole;
5-(N-benzyloxycarbonyl-(±)-para-iodophenylalaninamidomethyl)-3-bromo-4,5-dihydroisoxazole;
5-(N-2-(S)-(6methoxy-2-naphthyl)-propionyl-L-tyrosinamidomethyl)-5-(S)-3-bromo-4,5-dihydroisoxazole;
5-(N-α-benzyloxycarbonyl-L-glutamic acid α-amidomethyl)-3-chloro-4,5-dihydroisoxazole;
5-(N-para-methoxybenzyloxycarbonyl-L-tyrosinamidomethyl)-5-(S)-3-chloro-4,5-dihydroisoxazole;
5-(N-(2-(S)-(6-methoxy-2-naphthyl)-propionyl)-L-tyrosinamidomethyl) 5-(S)-3-chloro-4,5-dihydroisoxazole;
5-(N-(2-naphthyl-acetyl)-L-tyrosinamidomethyl-5-(S)-3-chloro-4,5-dihydroisoxazole;
5-(N-(1-naphthyl-acetyl)-L-tyrosinamidomethyl)-5-(S)-3-chloro-4,5-dihydroisoxazole;
5-(N-isobutyloxycarbonyl-L-phenylalaninamidomethyl)-3-bromo-4,5-dihydroisoxazole;
5-(N-succinyl-L-phenylalaninamidomethyl)-3-bromo-4,5-dihydroisoxazole;
5-(N-benzyloxycarbonyl-L-threonyl-L-phenylalaninamidomethyl)-3-bromo-4,5-dihydroisoxazole;
5-(N-cinnamoyl-L-phyenylalaninamidomethyl)3-bromo-4,5-dihydroisoxazole;
5-(N-(2(S)-6-methoxy-2-naphthylpropionyl)-L-phenylalaninamidomethyl)-3-bromo-4,5-dihydroisoxazole;
5-(N-(2(S)-6-methoxy-2-naphthylpropionyl)-L-phenylalaninamidomethyl)5-(R)-3-bromo-4,5-dihydroisoxazole;
5-(N-(2-(S)-6-methoxy-2-naphthylpropionyl)-L-phenylalaninamidomethyl)-5-(S)-3-bromo-4,5-dihydroisoxazole;
5-(N-adamantyloxycarbonyl-L-phenylalaninamidomethyl)-3-bromo-4,5-dihydroisoxazole;
5-(N-2-chlorobenzyloxycarbonyl-L-phenylalaninamidomethyl)-3-bromo-4,5-dihydroisoxazole;
5-(N-(4-methoxybenzyloxycarbonyl)-L-phenylalaninamidomethyl)-3-bromo-4,5-dihydroisoxazole;
5-(N-(4-methoxybenzyloxycarbonyl)-L-phenylalaminamidomethyl)-5-(R)-3-bromo-4,5-dihydroisoxazole;
5-(N-(4-methoxybenzyloxycarbonyl)-L-phenylalaninamidomethyl)-5-(S)-3-bromo-4,5-dihydroisoxazole;
5-(N-tertbutoxycarbonyl-glycyl-L-phenylalaninamidomethyl)-3-bromo-4,5-dihydroisoxazole;
5-(N-α-benzyloxycarbonyl-L-lysinamidomethyl)-3-bromo-4,5-dihydroisoxazole oxalic acid;
5-(glycyl-L-phenylalaninamidomethyl)-3-bromo-4,5-hydroisoxazole oxalate salt;
5-(N-(6-methoxy-2-naphthyl)acetyl-L-phenylalaninamidomethyl)-3-chloro-4,5-dihydrosoxazole; and
5-(N-(6-methoxy-2-naphthyl)acetyl-L-tyrosinamidomethyl)3-chloro-4,5-diydroisoxazole; or an optical isomer thereof.

7. A method according to claim 6 wherein the disease state in acne.

8. A method according to claim 6 wherein the disease state is psoriasis.

9. A method according to claim 6 wherein the disease state is cataracts.

10. A method of according to claim 6 wherein the compound is 5-(N-benzyloxycarbonyl-L-para-tyrosinamidomethyl)-5-(S)-3-chloro-4,5-dihydroisoxazole.

11. A method according to claim 7 wherein the compound is 5-(N-benzyloxycarbonyl-L-para-tyrosinamidomethyl)-5-(S)-3-chloro-4,5-dihydroisoxazole.

12. A method according to claim 8 wherein the compound is 5-(N-benzyloxycarbonyl-L-paratyrosinamidomethyl)-5-(S)-3-chloro-4,5-dihydroisoxazole.

13. A method according to claim 9 wherein the compound is 5-(N-benzyloxycarbonyl-L-paratyrosinamidomethyl)-5-(S)-3-chloro-4,5-dihydroisoxazole.

* * * * *